(12) United States Patent
Cathala et al.

(10) Patent No.: US 11,332,600 B2
(45) Date of Patent: May 17, 2022

(54) METHOD FOR PRODUCING NANOCELLULOSES FROM A CELLULOSE SUBSTRATE

(71) Applicant: INSTITUT NATIONAL DE LA RECHERCHE AGRONOMIQUE—INRA, Paris (FR)

(72) Inventors: Bernard Cathala, La Chapelle sur Erdre (FR); Ana Villares, Nantes (FR); Jean-Guy Berrin, Roquevaire (FR); Celine Moreau, Nantes (FR)

(73) Assignee: INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 293 days.

(21) Appl. No.: 15/577,964

(22) PCT Filed: Jun. 1, 2016

(86) PCT No.: PCT/FR2016/051306
§ 371 (c)(1),
(2) Date: Nov. 29, 2017

(87) PCT Pub. No.: WO2016/193617
PCT Pub. Date: Dec. 8, 2016

(65) Prior Publication Data
US 2018/0142084 A1   May 24, 2018

(30) Foreign Application Priority Data
Jun. 3, 2015 (FR) ...................... 1555049

(51) Int. Cl.
| | | |
|---|---|---|
| *C08L 1/02* | (2006.01) | |
| *D21C 5/00* | (2006.01) | |
| *D21C 9/00* | (2006.01) | |
| *B82Y 40/00* | (2011.01) | |
| *C12P 19/04* | (2006.01) | |
| *D21H 11/18* | (2006.01) | |
| *C08L 1/04* | (2006.01) | |
| *D21H 17/05* | (2006.01) | |
| *D21H 11/04* | (2006.01) | |
| *D21H 11/06* | (2006.01) | |
| *D21H 11/20* | (2006.01) | |
| *D21H 25/00* | (2006.01) | |

(52) U.S. Cl.
CPC ............. *C08L 1/02* (2013.01); *B82Y 40/00* (2013.01); *C08L 1/04* (2013.01); *C12P 19/04* (2013.01); *D21C 5/005* (2013.01); *D21C 9/007* (2013.01); *D21H 11/04* (2013.01); *D21H 11/06* (2013.01); *D21H 11/18* (2013.01); *D21H 11/20* (2013.01); *D21H 17/05* (2013.01); *D21H 25/005* (2013.01)

(58) Field of Classification Search
None
See application file for complete search history.

(56) References Cited

U.S. PATENT DOCUMENTS

| | | |
|---|---|---|
| 4,483,743 A | 11/1984 | Turbak et al. |
| 2002/0040134 A1 | 4/2002 | Ishihara et al. |

FOREIGN PATENT DOCUMENTS

| | | |
|---|---|---|
| WO | 2007/091942 A1 | 8/2007 |
| WO | 2014/029909 A1 | 2/2014 |
| WO | 2014/077854 A1 | 5/2014 |
| WO | 2014/085730 A1 | 6/2014 |

OTHER PUBLICATIONS

Morgenstern et al. Briefings in Functional Genomics, 2014, vol. 13, No. 6, pp. 471-481.*
Horn et al. Biotechnology for Biofuels. 2012, 5:45, pp. 1-12.*
Eibinger et al. "Cellulose surface degradation by a lytic polysaccharide monooxygenase and its effect on cellulase hydrolytic efficiency". The Journal of Biological Chemistry. Dec. 2014, vol. 289, No. 52, pp. 35929-36938.*
M. Eibinger et al: "Cellulose Surface Degradation by a Lytic Polysaccharide Monooxygenase and Its Effect on Cellulase Hydrolytic Efficiency", Journal of Biological Chemistry, vol. 289, No. 52, Dec. 26, 2014 (Dec. 26, 2014), US, pp. 35929-35938, XP055230517, ISSN: 0021-9258, DOI: 10.1074/jbc.M114.602227.
J. W. Agger et al: "Discovery of LPMO activity on hemicelluloses shows the importance of oxidative processes in plant cell wall degradation", Proceedings of the National Academy of Sciences, vol. 111, No. 17, Apr. 14, 2014 (Apr. 14, 2014), US, pp. 6287-6292, XP055242278, ISSN: 0027-8424, DOI: 10.1073/pnas.1323629111.
I. Morgenstern et al: "Fungal cellulose degradation by oxidative enzymes: from dysfunctional GH61 family to powerful lytic polysaccharide monooxygenase family", Briefings in Functional Genomics, Sep. 12, 2014 (Sep. 12, 2014), XP055145373, ISSN: 2041-2649, DOI: 10.1093/bfgp/elu032.
International Search Report, dated Sep. 2, 2016, from corresponding PCT/FR2016/051306 application.
Janardhnan, S. and Sain, M., "Isolation of Cellulose Microfibrils—An Enzymatic Approach," BioResources 1(2), 176-188, 2006.

(Continued)

*Primary Examiner* — Vera Afremova
(74) *Attorney, Agent, or Firm* — Nixon & Vanderhye

(57) ABSTRACT

Disclosed is a method for producing nanocelluloses from a cellulose substrate including cellulose fibers, the method including the following sequence of steps: —a step of enzymatic treatment of the cellulose substrate, by bringing same into contact with at least one cleaving enzyme, then—a step of mechanical treatment of the cellulose substrate subjected to the step of enzymatic treatment, in order to delaminate the cellulose fibres and obtain the nanocelluloses. The at least one cleaving enzyme is chosen from the enzymes belonging to the family of lytic polysaccharide monooxygenases (LPMOs) capable of achieving cleavage in the presence of an electron donor. Also disclosed are the nanocelluloses obtained according to the method.

17 Claims, 5 Drawing Sheets

(56) References Cited

OTHER PUBLICATIONS

Comeau, A. et al., "Functional Annotation of the Ophiostoma novo-ulmi Genome: Insights into the Phytopathogenicity of the Fungal Agent of Dutch Elm Disease," Genome Biol. Evol. 7(2): 410-430, Feb. 1, 2015.
Satyamurthy, P. et al., "Preparation and characterization of cellulose nanowhiskers from cotton fibres by controlled microbial hydrolysis," Carbohydrate Polymers 83 (2011) 122-129.
Vigneshwaran, N. et al., "Biological Synthesis of Nanocrystalline Cellulose by Controlled Hydrolysis of Cotton Fibers and Linters," in "Handbook of Polymer Nanocomposites. Processing, Performance and Application," Dec. 2, 2014.

\* cited by examiner

Figure 5
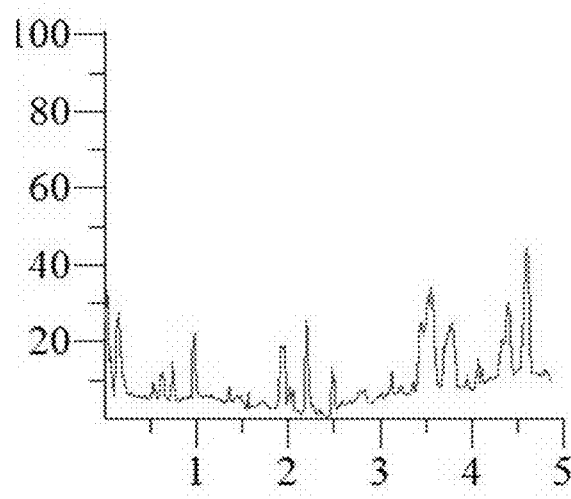
Figure 5A
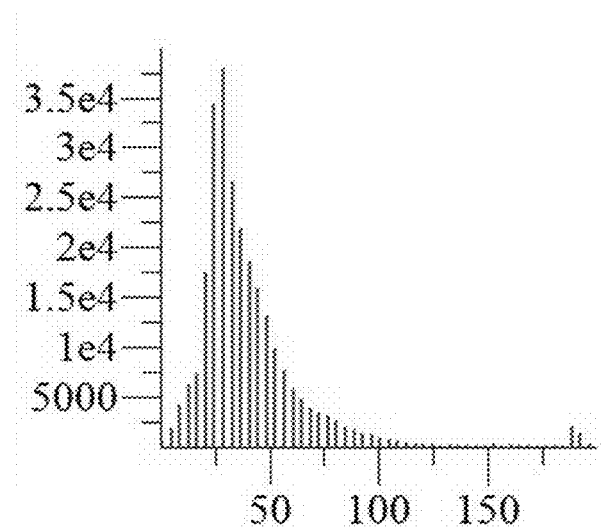
Figure 5B

METHOD FOR PRODUCING NANOCELLULOSES FROM A CELLULOSE SUBSTRATE

TECHNICAL FIELD TO WHICH THE INVENTION RELATES

The present invention relates, generally, to the field of nanocelluloses, and more particularly the processes for producing these nanocelluloses from a cellulose-based substrate.

TECHNICAL BACKGROUND

Cellulose is one of the most important natural polymers, a virtually inexhaustible raw material, and an important source of materials that are sustainable on the industrial scale.

To date, various forms of cellulose have been identified with a size of about one nanometer, denoted under the generic name of "nanocelluloses".

The properties of these nanocelluloses, in particular their mechanical properties, their ability to form films and their viscosity, gives them a major advantage in numerous industrial fields.

Nanocelluloses are thus used, for example, as a dispersant or stabilizing additive in the papermaking, pharmaceutical, cosmetics or food-processing industries. They are also part of the composition of paints and varnishes.

Nanocelluloses are also used in many devices that require a control of nanometric porosity, owing to their high specific surface area.

Finally, many nanocomposite materials based on nanocelluloses are currently being developed. This is because the notable mechanical properties of nanocelluloses, their dispersion on the nanometric scale and also their hydrophilic nature, give them excellent gas-barrier properties. These characteristics create in particular a considerable advantage for the production of barrier packagings.

On the basis of their sizes, functions and preparation methods, which themselves depend mainly on the cellulose-based source and on the treatment conditions, nanocelluloses can be classified mainly in two families: cellulose fibrils and cellulose nanocrystals.

Cellulose nanocrystals (also known as NCCs for "nanocrystalline celluloses") are generally obtained by hydrolysis with a strong acid under strictly controlled temperature, time and stirring conditions. Such a treatment makes it possible to attack the amorphous regions of the fibers while at the same time leaving the more resistant crystalline regions intact. The suspension obtained is then washed by centrifugations and successive dialyses in distilled water. The NCCs most conventionally obtained have a length of a few tens of nanometers to approximately 1 µm (in particular from 40 nm to 1 µm and preferably from 40 nm to 500 nm), and a diameter ranging from 5 to 70 nm, preferably less than 15 nm (typically from 5 to 10 nm).

Cellulose fibrils, commonly denoted cellulose microfibrils (also referred to as MFC for "microfibrilated cellulose") or cellulose nanofibrils (NFC for "nanofibrilated cellulose") are typically isolated from cellulose-based materials derived from biomass, by mechanical processes which make it possible to delaminate the cellulose fibers and to release the cellulose fibrils.

For example, document U.S. Pat. No. 4,483,743 describes a process for producing microfibrilated cellulose, which involves passing a liquid suspension of cellulose through a high-pressure Gaulin homogenizer. Repeated passes of the cellulose suspension make it possible to obtain microfibrils which typically have a width ranging from 25 to 100 nm and a much longer length.

In general, the mechanical processes for obtaining cellulose fibrils have the drawback of consuming large amounts of energy. By way of example, it has been evaluated that the use of a homogenizer causes an energy consumption of about 70 000 kWh/t. This high energy consumption, and consequently the high costs of producing nanocelluloses, therefore remain a considerable impediment to their industrial development.

Various cellulose fiber pretreatment strategies have thus been developed in order to reduce the energy consumption required for their mechanical delamination.

A first pretreatment strategy, described for example in application WO 2007/091942, consists in pretreating the cellulose fibers with cellulases so as to destroy the fiber before the application of the mechanical treatment by homogenization.

However, this enzymatic pretreatment is extremely changeable depending on the condition of the fiber and in particular depending on the prior thermochemical history of the fiber.

Furthermore, the quality of the nanocelluloses obtained (in particular the dispersion state and especially the lateral size of the nanofibrils which conditions the wear properties and the energy yields) are very variable.

A second pretreatment strategy is based on a chemical step of oxidation of the cellulose fibers (for example, Saito et al., Biomacromolecules, Vol. 8, No. 8, 2007, pp. 2485-2491).

Typically, the fibers are oxidized with an oxidizing agent such as sodium hypochlorite catalyzed by the 2,2,6,6-tetramethylpiperidine-1-oxyl ("TEMPO") radical, before undergoing the abovementioned mechanical treatment.

The oxidative treatment converts the primary alcohol function in the $O_6$ position of the glucose unit of the cellulose into a carboxylate function, which results in the introduction of charges at the surface of the cellulose fibers. These charges create electrostatic repulsions which facilitate the delamination and which increase its efficiency.

However, the removal of the reaction products results in large amounts of highly polluted effluents. In addition, reactant residues persist in the final product and continue to react, altering, in the end, the properties of the nanocelluloses.

Thus, despite the new pretreatment strategies developed, the costs of nanocellulose production remain high, the yields uncertain, and the quality and the properties are variable.

It thus remains necessary to provide new processes for obtaining nanocelluloses, with a lower energy consumption and which are simple and reproducible, according to a route that is not toxic or has low toxicity.

SUBJECT OF THE INVENTION

In order to overcome the abovementioned drawbacks of the prior art, the present invention provides a process for producing nanocelluloses which is based on a step of pretreating cellulose fibers with at least one enzyme belonging to the family of lytic polysaccharide monooxygenases, commonly denoted "LPMOs".

More particularly, according to the invention, a process is provided for producing nanocelluloses from a cellulose-based substrate comprising cellulose fibers, said process comprising the following successive steps:
at least one step of enzymatic treatment of said cellulose-based substrate, by bringing it into contact with at least one cleavage enzyme, then at least one step of mechanical treatment of said cellulose-based substrate subjected to said at least one step of enzymatic treatment, in order to delaminate the cellulose fibers and to obtain said nanocelluloses, characterized in that said at least one cleavage enzyme is chosen from the enzymes belonging to LPMO family.

Typically, LPMOs are capable of performing an oxidative cleavage of cellulose fibers, advantageously of the glucose rings of cellulose fibers, in the presence of an electron donor.

Without being limited by any theory, the action of LPMOs facilitates the production of nanocellulose through two actions:
- the cleavage of the cellulose-based chains causes fragilities within the fibers, facilitating the mechanical delamination,
- the formation of oxidation products makes it possible to introduce charged chemical functions on the surface of the fibers, inducing electrostatic repulsions.

Again without being limited by any theory, the consequence of these combined structural modifications is to promote the separation of the fibers until nanometric dispersion is obtained and to form nanocelluloses (fibrils or nanocrystals) which have new functionalities (degree of charges, chemical functions not currently available).

Other nonlimiting and advantageous characteristics of the production process in accordance with the invention, taken individually or according to all the technically possible combinations, are also described hereinafter and also in the detailed description of the invention.

The electron donor can be chosen from ascorbate, gallate, catechol, reduced glutathione, lignin fragments and fungal carbohydrate dehydrogenases (in particular glucose dehydrogenases and cellobiose dehydrogenases).

Preferably, the LPMOs are chosen from enzymes capable of carrying out a cleavage of the cellulose by oxidation of at least one of the carbon atoms in position(s) $C_1$, $C_4$ and $C_6$ of the glucose ring. More preferably, the LPMOs are chosen from enzymes capable of carrying out a cleavage of the cellulose by oxidation of at least one of the carbon atoms in position(s) $C_1$ and/or $C_4$, optionally in combination with $C_6$, of the glucose ring.

The LPMOs can be chosen from the families of fungal enzymes AA9 (formerly known as GH61) and of bacterial enzymes AA10 (formerly known as CBM33) of the CAZy classification (www.cazy.org). In particular, the LPMOs can be chosen from the LPMOs derived from *Podospora anserina* and preferably from PaLPMO9A (Genbank CAP68375), PaLPMO9B (Genbank CAP73254), PaLPMO9D (Genbank CAP66744), PaLPMO9E (Genbank CAP67740), PaLPMO9F (Genbank CAP71839), PaLPMO9G (Genbank CAP73072), and PaLPMO9H (Genbank CAP61476).

According to the embodiments of the invention, the cellulose-based substrate is obtained from wood, from a cellulose-rich fibrous plant, from beetroot, from citrus fruits, from annual straw plants, from marine animals, from algae, from fungi or from bacteria.

Preferably, the cellulose-based substrate is chosen from chemical papermaking pulps, preferably chemical wood papermaking pulps, more preferably at least one of the following papermaking pulps:
- bleached pulps,
- semi-bleached pulps,
- raw pulps,
- bisulfite pulps,
- sulfate pulps,
- sodium hydroxide pulps,
- kraft pulps.

Said at least one step of mechanical treatment generally comprises at least one of the following mechanical treatments:
- a homogenization treatment,
- a microfluidization treatment,
- an abrasion treatment,
- a cryomilling treatment.

The process can also comprise a post-treatment step, for example an acid treatment, an enzymatic treatment, an oxidation, an acetylation, a silylation, or else a derivatization of certain chemical groups borne by the nanocelluloses.

The invention also relates to the nanocelluloses obtained by carrying out the process of the invention.

Typically, the nanocelluloses obtained consist of cellulose nanofibrils and/or of cellulose nanocrystals.

Preferably, the nanocelluloses comprise glucose rings of which at least one carbon atom is oxidized in position(s) $C_1$ and/or $C_4$, or even also in position $C_6$.

DESCRIPTION OF THE DRAWINGS

FIG. 5: Analysis of the AFM photos for the PaLPMO9H enzyme, so as to characterize the height profile (FIG. 5A) and the size distribution (FIG. 5B) of the nanocelluloses. Legend to FIG. 5A: example of a height profile obtained on the surface, width (x, μm) versus height (y, nm); legend to FIG. 5B: histogram of height distribution with height (x, nm) versus number (y).

DETAILED DESCRIPTION

Figure 1:
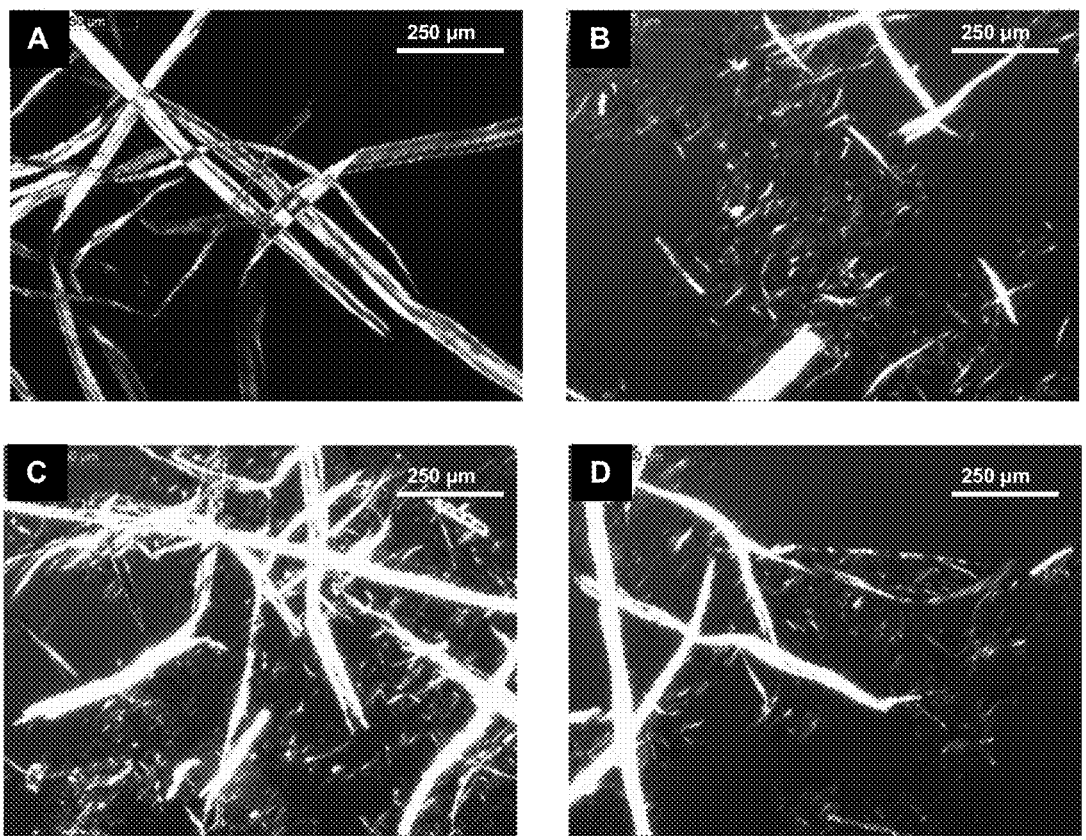
FIG. 1: Appearance of kraft fibers of cellulose that have been treated with the PaLPMO9H enzyme according to various enzyme/substrate ratios and subjected to a weak mechanical treatment with a homogenizer-disperser of the Ultra-Turrax type and an ultrasonic treatment. Optical microscopy images of the fibers not treated (control) with the enzyme (A) or treated with enzyme/substrate ratios of 1:50 (B); 1:100 (0); and 1:500 (D).

The description which follows, in combination with the Experimental Results given by way of nonlimiting examples, will provide a clear understanding of what the invention consists of and how it can be carried out.

General Definitions

The present invention relates to a process for producing nanocelluloses, in particular cellulose fibrils and/or cellulose nanocrystals, from a cellulose-based substrate.

The term "cellulose" is intended to mean a linear homopolysaccharide derived from biomass (encompassing organic matter of plant origin, algae included, cellulose of animal origin and also cellulose of bacterial origin) and consisting of units (or rings) of glucose (D-anhydroglucopyranose—AGU for "anhydro glucose unit") which are linked to one another by β-(1-4) glycosidic bonds. The repeat unit is a glucose dimer also known as cellobiose dimer.

AGUs have 3 hydroxyl functions: 2 secondary alcohols (on the carbons in positions 2 and 3 of the glucose ring) and a primary alcohol (on the carbon in position 6 of the glucose ring).

These polymers link together via intermolecular bonds of hydrogen bond type, thus conferring a fibrous structure on the cellulose. In particular, the linking of cellobiose dimers forms an elementary cellulose nanofibril (the diameter of which is approximately 5 nm). The linking of elementary nanofibrils forms a nanofibril (the diameter of which generally ranges from 50 to 500 nm). The arranging of several of these nanofibrils then forms what is generally referred to as a cellulose fiber.

The term "nanocelluloses" denotes the various forms of cellulose having a size of about one nanometer. This encompasses in particular, according to the invention, two nanocellulose families: cellulose nanocrystals and cellulose fibrils.

The terms "cellulose fibrils", "(cellulose) nanofibrils", "(cellulose) nanofibers", "nanofibrilated cellulose", "(cellulose) microfibrils", "microfibrilated cellulose", and "cellulose nanofibrils" are synonymous. In the remainder of the present application, the term "cellulose nanofibrils" (NFCs) will be used generically.

Each cellulose nanofibril contains crystalline parts stabilized by a solid network of inter-chain and intra-chain hydrogen bonds. These crystalline regions are separated by amorphous regions.

Elimination of the amorphous parts of cellulose nanofibrils makes it possible to obtain cellulose nanocrystals (NCCs).

NCCs advantageously comprise at least 50% of crystalline part, more preferably at least 55% of crystalline part. They generally have a diameter ranging from 5 to 70 nm (preferably less than 15 nm) and a length ranging from 40 nm to approximately 1 μm, preferably ranging from 40 nm to 500 nm.

The terms "cellulose nanocrystals", "nanocrystalline cellulose", "cellulose whiskers", "microcrystals" or "nanocrystal cellulose" are synonymous. In the remainder of the present application, the term "cellulose nanocrystals" (NCCs) will be used generically.

In the case of bacterial cellulose, nanofibrils, or ribbons, of bacterial cellulose generally have a length of several micrometers and a width ranging from 30 to 60 nm, in particular from 45 to 55 nm.

Process According to the Invention

The process for producing nanocelluloses, according to the invention, comprises the following successive steps:

at least one step of enzymatic treatment of a cellulose-based substrate comprising cellulose fibers, by bringing it into contact with at least one cleavage enzyme belonging to the family of lytic polysaccharide monooxygenases (LPMOs), then at least one step of mechanical treatment of said cellulose-based substrate subjected to said at least one step of enzymatic treatment, in order to delaminate said cellulose fibers and to obtain said nanocelluloses.

One or more, and in particular at least two, steps of enzymatic treatment can be carried out according to the process of the invention, prior to said at least one step of mechanical treatment. For example, at least two steps of enzymatic treatment can be carried out successively, prior to said at least one step of mechanical treatment.

At least one step of enzymatic treatment can also be carried out after said at least one step of mechanical treatment.

When several steps of enzymatic treatment are carried out, the treatment conditions (time, LPMO(s) chosen, enzyme/cellulose ratio, etc.) can be identical to or different than one another.

Typically, said at least one step of enzymatic treatment, optionally followed by at least one step of mechanical treatment, can be repeated, as described above, until complete delamination of the cellulose fibers is obtained.

For example, the process of the invention can comprise at least two successive treatment cycles, each treatment cycle comprising at least one step of enzymatic treatment of the cellulose-based substrate, followed by at least one step of mechanical treatment of said substrate.

Without being limited by any theory, the combination according to the invention (i) of an enzymatic treatment with at least one LPMO and (ii) of a mechanical delamination treatment makes it possible to obtain nanocelluloses of which the structural characteristics and the mechanical properties are entirely different than the nanocelluloses that exist in the prior art.

Again without being limited by any theory, the process of the invention makes it possible to obtain nanocelluloses simply and reproducibly. Preferably, the size and the mechanical properties of these nanocelluloses are uniform.

Cellulose-Based Substrate

The cellulose-based substrate can be obtained according to the invention from any matter of the biomass (encompassing organic matter of plant origin, algae included, animal origin or fungal origin) comprising cellulose-based fibers (that is to say cellulose fibers).

The cellulose-based substrate is advantageously obtained from wood (of which cellulose is the main component), but also from any cellulose-rich fibrous plant, for instance cotton, flax, hemp, bamboo, kapok, coconut fibers (coir), ramie, jute, sisal, raffia, papyrus and certain reeds, sugarcane bagasse, beetroot (and in particular beetroot pulp), citrus fruits, corn stalks or sorghum stalks, or else annual straw plants.

The cellulose-based substrates can also be obtained from marine animals (such as tunicates for example), algae (for instance *Valonia* or *Cladophora*) or bacteria for bacterial cellulose (for instance bacterial strains of *Gluconacetobacter* types).

Depending on the applications, cellulose from primary walls, for instance the parenchyma of fruits (for example beetroots, citrus fruits, etc.), or from secondary walls, for instance wood, will be chosen.

The cellulose-based substrate advantageously consists of a cellulose-based material prepared by chemical or mechanical means from any cellulose-based source as mentioned above (and in particular from wood).

The cellulose-based substrate is advantageously in the form of a suspension of cellulose fibers in a liquid medium (preferably an aqueous medium), or of a cellulose pulp.

The cellulose pulps can be conditioned in the "dry" state, that is to say typically in a state of dryness greater than or equal to 80%, in particular greater than or equal to 90%. The cellulose pulp can subsequently be redispersed in an aqueous medium by mechanical treatment.

Preferably, the cellulose-based substrate contains at least 90%, in particular at least 95% and preferably 100% of cellulose fibers.

Preferably, the cellulose-based substrate is suitable for the production of paper or of a cellulose-based product. The cellulose-based substrate is thus preferably chosen from papermaking pulps (or paper pulp), and in particular chemical papermaking pulps.

Generally, the cellulose pulp and in particular the papermaking pulp can contain, in combination with the cellulose fibers, hemicellulose and lignin. Preferably, the cellulose pulp contains less than 10% and in particular less than 5% of lignin and/or of hemicellulose.

Preferably, the chemical papermaking pulps contain virtually exclusively, or even exclusively, cellulose fibers.

The papermaking pulp can be chosen from at least one of the following papermaking pulps: bleached pulps, semi-bleached pulps, raw pulps, (raw or bleached) bisulfite pulps, (raw or bleached) sulfate pulps, (raw or bleached) sodium hydroxide pulps and kraft pulps.

It is also possible to use pulps to be dissolved, that have a low proportion of hemicellulose, preferably less than 10% and in particular less than or equal to 5%.

Preferably, the papermaking pulps used in a process of the invention are wood pulps, in particular chemical papermaking pulps of wood.

Lytic Polysaccharide Monooxydenases—LPMOs

The cellulose-based substrate is thus subjected to at least one step of pretreatment with at least one cleavage enzyme belonging to the lytic polysaccharide monooxygenase (LPMO) family.

LPMOs are mononuclear type II copper enzymes. They have common structural characteristics, in particular:
  a planar surface with an active site located close to its center and
  a highly conserved binding site for a type II copper ion exposed at the surface of the protein.

The interaction between the LPMO enzyme and the surface of the cellulose occurs by means of the planar face of the LPMO enzyme and involves interactions with polar aromatic residues. The LPMOs that can be used according to the invention are defined by their capacity to catalyze an oxidative cleavage of the cellulose fibers of the cellulose-based substrate, by oxidation of at least one of the carbon atoms in positions $C_1$, $C_4$ and $C_6$ of a glucose ring of said cellulose fibers.

The principle of the oxidative cleavage carried out by the LPMOs involves the activation of a C—H group followed by a dioxygen ($O_2$)-dependent cleavage, thus producing oligomers that are oxidized on at least one of the carbons in positions $C_1$, $C_4$ and $C_6$.

The LPMO(s) used are capable of catalyzing a cleavage of the cellulose fibers by oxidation of at least one of the carbons chosen from the carbons in positions $C_1$ and/or $C_4$ and/or $C_6$ of a glucose ring of the cellulose. The oxidative cleavage results in the formation of carboxyl groups at the surface of the cellulose fibers:

the oxidative cleavage in position $C_1$ of a glucose ring of a cellobiose unit leads to the formation of a lactone, which is spontaneously hydrolyzed to aldonic acid, and
the oxidative cleavage in position $C_4$ of a glucose ring of a cellobiose unit results in the formation of a ketoaldose.

The oxidation of the alcohol group in position $C_6$ of a glucose ring of a cellobiose unit results in the formation of a carbonyl group.

In some embodiments, the LPMO(s) used catalyze(s) a cleavage of the cellulose fibers by oxidation of at least one of the carbons chosen from the carbons in position(s) $C_1$ and/or $C_4$ of a glucose ring of the cellulose, optionally in combination with the carbon in position $C_6$.

LPMOs catalyze the oxidative cleavage of a cellobiose unit in the presence of an external electron donor.

This electron donor, generally a molecule of low molecular weight, is chosen from ascorbate, reduced glutathione, gallate, catechol, lignin fragments, or else an enzyme of the carbohydrate dehydrogenase family.

Preferably, the carbohydrate dehydrogenases are chosen from fungal enzymes, in particular cellobiose dehydrogenases (CDHs).

CDHs (or cellobiose oxidoreductases—EC 1.1.99.18) catalyze the [cellobiose+electron acceptor<=>cellobiono-1, 5-lactone+reduced acceptor] reaction. They are fungal hemoflavoenzymes belonging to the glucose-methanol-choline (GMC) oxidoreductase superfamily. CDHs are monomeric enzymes bearing two prosthetic groups, a heme group b and a flavin adenine dinucleotide. The flavoprotein domain of CDHs catalyzes the two-electron oxidation of cellobiose to lactone using an electron acceptor. This electron acceptor can for example be chosen from dioxygen, quinones and phenoxy radicals or LPMOs.

The activity of a CDH enzyme can be determined according to the reduction of the reagent 2,6-dichlorophenol indophenol (DCPIP) in a sodium acetate buffer containing cellobiose (Bey et al., 2011, Microb. Cell Fact. 10:113).

Examples of CDHs that can be used in combination with at least one LPMO enzyme and which also act as an electron donor can be chosen from the CDHs originating from *Pycnoporus cinnabarinus*, *Humicola insolens*, *Podospora anserina*, or *Myceliophthora thermophila*.

More preferably, an LPMO enzyme for which a cellulolytic activity (that is to say an activity that catalyzes the oxidative cleavage of the cellulose) has been identified is used. The oxidative cleavage activity of LPMOs on a cellulose-based substrate can be tested in cleavage tests as described in the Example section of the present application.

More specifically, the LPMOs used in the invention are advantageously chosen from enzymes said to have "auxiliary activity" (AA) according to the classification established in the CAZy database, relating to enzymes that are active on carbohydrates (CAZy—Carbohydrate Active enZyme database—http://www.cazy.org/—see also Levasseur et al., Biotechnology for Biofuels 2013, 6: 41).

More preferably, the step of enzymatic treatment is carried out with at least one enzyme chosen from the LPMO enzymes of the families referred to as AA9, AA10, AA11 and AA13, according to the classification established in the CAZy database.

The LPMO enzyme according to the invention can contain a carbohydrate binding protein module specific for cellulose of CBM1 type according to the CAZy classification.

The enzymes listed in the present application are identified by the Genbank reference (identifying a genetic sequence) and the Uniprot reference when the latter is available (identifying a protein sequence—see table 1). By default, the reference indicated between parentheses for each enzyme corresponds to the "Genbank" reference.

Preferably, at least one enzyme of the AA9 family and/or at least one enzyme of the AA10 family of the CAZy classification is (advantageously exclusively) used.

The enzymes of the AA9 family, listed in table 1 hereinafter, are fungal enzymes widely distributed in the genome of most ascomycetes and in some basidiomycetes (fungi).

Generally, the enzymes of the AA9 family were initially classified in the family of glycoside hydrolases 61 (GH61) of the CAZy classification. Specific analyses have since shown that the endoglucanase activity of the AA9 enzymes is weak, or even nonexistent (Morgenstern I et al., Briefings in Functional Genomics vol. 3(6P): 471-481).

Preferably, LPMOs of which the endoglucanase activity is not significant or is inexistent are used.

The copper ion of the LPMOs of the AA9 family is bound to the protein according to a hexacoordination model involving at least 2 conserved histidine residues and water molecules.

The enzymes of the AA9 family catalyze an oxidative cleavage of the cellobiose unit on the carbon in position $C_1$ and/or $C_4$, preferably on the carbon in position $C_1$ or $C_4$. Some enzymes (*T. aurantiacus* TaGH61A (G3XAP7) and *Podospora anserina* PaGH61 B (B2AVF1)) could catalyze an oxidative cleavage of the cellobiose on a carbon in position $C_6$.

The LPMOs of the AA9 family that is expressed in fungi generally exhibits a post-translational modification consisting of a methylation of the N-terminal histidine residue.

Preferably, LPMOs of the AA9 family comprising at least one CBM1 or CBM18 domain (CBM for "carbohydrate binding module") in the N-terminal position are used. These enzymes then comprise a planar surface made up of several polar aromatic residues forming a domain of CBM1 or CBM18 type.

More preferably, said at least one LPMO of the AA9 family is derived from *Podospora anserina* and/or from *Neurospora crassa*.

The enzymes of the AA9 family derived from *Podospora anserina* are typically chosen from the group consisting of PaLPMO9A (CAP68375), PaLPMO9B (CAP73254), PaLPMO9D (CAP66744), PaLPMO9E (CAP67740), PaLPMO9F (CAP71839), PaLPMO9G (CAP73072) and PaLPMO9H (CAP61476).

Preferably, the PaLPMO9E (CAP67740) and/or PaLPMO9H (CAP61476) enzymes are used.

The enzymes of the AA9 family derived from *Neurospora crassa* are typically chosen from the group consisting of NcLPMO9C (EAA36362), NcLPMO9D (EAA32426/CAD21296), NcLPMO9E (EAA26873), NcLPMO9F (EAA26656/CAD70347), NcLPMO9M (EAA33178), NcU00836 (EAA34466), NcU02240 (EAA30263) and NcU07760 (EAA29018).

The enzymes of the AA10 family (CAZy classification) were formerly classified in the CBM33 family (or "carbohydrate binding module family 33") of the CAZy classification.

The LPMO family AA10 comprises, at the current time, more than about a thousand enzymes, identified particularly in bacteria, but also in some eukaryotes and also in some viruses.

The LPMOs of the AA10 family have a structure similar to that of the enzymes of the AA9 family and in particular at least one conserved tyrosine residue in the N-terminal position, which is involved in the binding with the copper ion. However, in most LPMOs of the AA10 family, one of the other tyrosine residues involved in the axial binding of the copper ion is replaced with a phenylalanine residue. For these enzymes, an oxidative activity has been demonstrated on chitin and on cellulose.

Preferably, the enzymes of the AA10 family are multimodular and comprise a CBM domain in the N-terminal position. These domains are typically CBM2, CBM5, CBM10 and CBM12 domains and also fibronectin type III modules.

The AA11 family is characterized by enzymes which carry out an oxidative cleavage in position $C_1$ on chitin. The enzyme of *Aspergillus oryzae* will preferably be chosen (see also Hemsworth et al., Nature Chemical Biology 2014(10): 122-126—Discovery and characterization of a new family of lytic polysaccharide monooxygenases).

The AA13 family is characterized by enzymes which carry out an oxidative cleavage in position $C_1$ on starch. The enzyme of *Aspergillus nidulans* will preferably be chosen (Lo Leggio et al., Nat Commun. 2015(22) 6: 5961—Structure and boosting activity of a starch-degrading lytic polysaccharide monooxygenase).

Generally, the step of enzymatic treatment is carried out by means of at least one LPMO enzyme listed in table 2 hereinafter.

In certain embodiments of the process of the invention, said at least one enzyme of the LPMO family (advantageously of the AA9 family and/or of the AA10 family) is used in combination with at least one cellulase.

The cellulase is advantageously chosen from at least one endoglucanase (for example one endoglucanase) and/or at least one carbohydrate dehydrogenase (advantageously one cellobiose dehydrogenase (CDH)). The carbohydrate dehydrogenases can act as an electron donor for the LPMOs.

In practice, said at least one LPMO enzyme used is advantageously purified from a culture supernatant of a fungus and/or produced in a heterologous system, in particular in a bacterium, a fungus or a yeast, for example in the *Pichia pastoris* yeast.

Said at least one LPMO enzyme is mixed with the cellulose-based substrate, so as to allow said at least one enzyme to be brought into contact with the cellulose fibers.

The step of enzymatic treatment is preferably carried out with gentle stirring, so as to ensure good dispersion of the enzymes within the fibers. This step of enzymatic treatment is for example carried out for a period ranging from 24 h to 72 h (preferably for 48 h).

Preferably, the step of enzymatic treatment is carried out at a temperature ranging from 30 to 45° C.

According to the invention, said at least one LPMO enzyme can be added to the cellulose-based substrate according to an enzyme/cellulose ratio ranging from 1:1000 to 1:50, in particular from 1:500 to 1:50 or from 1:100 to 1:50 or else from 1:1000 to 1:500, from 1:500 to 1:100.

Preferably, said at least one LPMO enzyme is used at a concentration ranging from 0.001 to 10 g/l, in particular from 0.1 to 5 g/l, and more preferably from 0.5 to 5 g/l.

According to one particular embodiment, the cellulose-based substrate is subjected to at least two (or even only to two) successive steps of enzymatic treatment (in series, advantageously separated by a rinsing step).

The LPMO(s) used during each of these steps of enzymatic treatment is (are) identical or different; the conditions (in particular the enzyme/substrate ratio) are identical or different between these successive steps.

In this case, the examples demonstrate that the fibers are entirely destructured, including at low enzyme/cellulose ratios.

Step(s) of Mechanical Treatment(s)

The pretreated cellulose-based substrate is then subjected to at least one step of mechanical treatment which is intended to delaminate the cellulose fibers in order to obtain nanocelluloses.

The delamination (also referred to as "fibrillation" or "defibrillation") consists in separating the cellulose fibers into nanocelluloses, via a mechanical phenomenon.

As demonstrated through the examples below, the oxidative cleavage of the cellulose fibers, catalyzed by said at least one LPMO, facilitates the delamination of these cellulose fibers during the step of mechanical treatment.

This step of mechanical delamination of the cellulose fibers can then be carried out under conditions that are less drastic and therefore less costly in terms of energy. Moreover, the use of LPMOs according to the invention makes it possible to introduce into the cellulose fibers charged groups which create electrostatic repulsions, without contamination with treatment reagents, such as when TEMPO reagents are used.

The mechanical treatments intended to delaminate cellulose fibers are known to those skilled in the art and can be implemented in the process of the invention.

Generally, mention may be made of weak mechanical treatments with a homogenizer-disperser (for example of the Ultra-Turrax type) and/or ultrasonic treatments.

Reference may also for example be made to the document of Lavoine N et al. (Carbohydrate Polymers, 2012, (92): 735-64) which describes in particular (pages 740 to 744) mechanical treatments for preparing microfibrilated cellulose (for example cellulose nanofibrils).

Typically, a mechanical treatment can be chosen from mechanical homogenization, microfluidization, abrasion or cryomilling treatments.

The homogenization treatment involves passing the pretreated cellulose-based substrate, typically a cellulose pulp or a liquid suspension of cellulose, through a narrow space under high pressure (as described for example in patent U.S. Pat. No. 4,486,743).

This homogenization treatment is preferably carried out by means of a homogenizer of Gaulin type. In such a device, the pretreated cellulose-based substrate, typically in the form of a cellulose suspension, is pumped at high pressure and distributed through an automatic valve with a small orifice. A rapid succession of openings and closings of the valve subjects the fibers to a considerable drop in pressure (generally of at least 20 MPa) and to a high-speed shear action followed by a high-speed deceleration impact. The passing of the substrate through the orifice is repeated (generally from 8 to 10 times) until the cellulose suspension becomes stable. In order to maintain a product temperature in a range of from 70 to 80° C. during the homogenization treatment, cooling water is generally used.

This homogenization treatment can also be carried out by means of a device of the microfluidizer type (see for example Sisqueira et al. Polymer 2010 2(4): 728-65). In such a device, the cellulose suspension passes through a typically "z"-shaped thin chamber (the dimensions of the channel of which are generally between 200 and 400 μm) under high pressure (approximately 2070 bar). The high shear rate which is applied (generally greater than $10^7.s^{-1}$) makes it possible to obtain very fine nanofibrils. A variable number of passes (for example from 2 to 30, in particular from 10 to 30 or from 5 to 25, and in particular from 5 to 20) with chambers of different sizes can be used, in order to increase the degree of fibrillation.

The abrasion or milling treatment (see for example Iwamoto S et al., 2007 Applied Physics A89(2): 461-66) is based on the use of a milling device capable of exerting shear forces provided by milling stones.

The pretreated cellulose-based substrate, generally in the form of a cellulose pulp, is passed between a static milling stone and a rotating milling stone, typically at a speed of about 1500 revolutions per minute (rpm). Several passes (generally between 2 and 5) may be required in order to obtain fibrils of nanometric size.

A device of mixer type (for example as described in Unetani K et al., Biomacromolecules 2011, 12(2), pp. 348-53) can also be used to produce microfibrils from pretreated cellulose-based substrate, for example from a suspension of wood fibers.

The cryomilling (or cryocrushing) treatment (Dufresne et al., 1997, Journal of Applied Polymer Science, 64(6): 1185-94) consists in milling a suspension of pretreated cellulose-based substrate frozen beforehand with liquid nitrogen. The ice crystals formed inside the cells cause the cell membranes to explode and release wall fragments. These processes are generally used for the production of cellulose microfibrils from agricultural products or residues.

Step(s) of Post-Treatment of the Cellulose-Based Substrate

In certain embodiments, the production process comprises at least one step of post-treatment of the cellulose-based substrate, carried out after said substrate has been subjected to the mechanical treatment.

Generally, said at least one post-treatment step aims to increase the degree of fibrillation of the nanocelluloses obtained and/or to confer new mechanical properties on said nanocelluloses, as a function of the applications envisioned.

Said at least one post-treatment step can in particular be chosen from an acid treatment, an enzymatic treatment, an oxidation, an acetylation, a silylation, or else a derivatization of certain chemical groups borne by the microfibrils. Reference may also be made, for example, to the document by Lavoine N et al (Carbohydrate Polymers, 2012, (92): 735-64) which describes in particular (point 2.3, pages 747 to 748) post-treatments that can be combined with various pretreatments and mechanical treatments of the cellulose fibers.

Nanocelluloses According to the Invention

The process according to the invention thus makes it possible to obtain nanocelluloses, in particular cellulose nanocrystals and/or cellulose nanofibrils.

Contrary to the NFCs obtained after oxidation by chemical reagents of TEMPO type, the nanocelluloses obtained by means of the process of the invention are devoid of oxidation reagent residues (namely, for example, sodium bromide, sodium hypochlorite, sodium chlorite, the (2,2,6,6-tetramethylpiperidin-1-yl)oxyl radical (TEMPO), derivatives or analogs).

Preferably, at the end of the process according to the invention, the nanocelluloses comprise at least one glucose ring (typically several glucose rings) of which at least one of the carbon atoms in positions $C_1$ and/or $C_4$, or even also $C_6$, is oxidized by an oxidative cleavage phenomenon.

The nanocelluloses according to the invention thus comprise glucose rings which are:
  monooxidized on the carbon atom in position $C_1$, and/or
  monooxidized on the carbon atom in position $C_4$, and/or
  doubly oxidized on the atoms in positions $C_1$ and $C_4$.

These glucose rings, oxidized on the atoms in positions $C_1$ and/or $C_4$, can also comprise an oxidized carbon atom in position $C_6$.

The term "oxidized carbon atom" is intended to mean in particular a carbon atom which comprises a carbonyl function, and advantageously also a carboxyl function.

The nanocelluloses according to the invention are thus advantageously negatively charged, because of the presence of various surface functions including carboxylate functions on the carbons in positions $C_1$ and/or $C_4$ (contrary to the TEMPO process which results in a specific oxidation of the carbon in position $C_6$).

Experimental Results

1. Tests for cleavage of the cellulose by an LPMO enzyme can be carried out according to the following protocol:

The cleavage test is carried out at a volume of 300 µl of liquid containing 4.4 µM of LPMO enzyme and 1 mM of ascorbate and 0.1% (weight/volume) of powder of phosphoric acid-swollen cellulose (PASO—prepared as described in Wood T M, *Methods Enzym* 1988, 160: 19-25) in 50 mM of a sodium acetate buffer at pH 4.8 or 5 µM of cellooligosaccharides (Megazyme, Wicklow, Ireland) in 10 mM of sodium acetate buffer at pH 4.8.

The enzymatic reaction is carried out in a 2 ml tube incubated in a thermomixer (Eppendorf, Montesson, France) at 50° C. and 580 rpm (revolutions per minute).

After incubation for 16 h, the sample is brought to 100° C. for 10 minutes in order to stop the enzymatic reaction, then centrifuged at 16 000 revolutions per minute (rpm) for 15 minutes at 4° C. in order to separate the solution fraction from remainder insoluble fraction.

The cleaved products obtained can be analyzed by ion exchange chromatography and/or by mass spectrometry (MALDI-TOF).

2. Preliminary tests were carried out in order to demonstrate the efficiency of the process for producing nanocellulose according to the invention.

These tests were carried out on a papermaking fiber (cellulose kraft fibers) by means of LPMO enzyme of the AA9 family derived from *Podospora anserina* (PaLPMO9E (Genbank CAP67740) and/or PaLPMO9H (Genbank CAP61476)) and produced in a heterologous system in yeast (*Pichia pastoris*).

The fibers are brought into contact with the enzymes (at a concentration of 1 g/l and according to enzyme/cellulose ratios of 1:50, 1:100, 1:500 and 1:1000) and with ascorbate (2 mM) and then subjected to gentle stirring for 48 hours at 40° C.

The treated fibers are then subjected to a mechanical action with a homogenizer-disperser (Ultra-Turrax power 500 W, maximum speed for 3 minutes), followed by an ultrasonic treatment for 3 minutes.

Compared with the substrates not treated with the enzyme, it is observed that the defibrillation is facilitated for all of the enzyme/cellulose ratios used (FIG. 1B-D—the photos show, qualitatively, the defibrillation).

In the absence of enzymes, the fibers remain intact and no defibrillation is noted (see the non-treated control fibers, FIG. 1A).

The dispersions were then analyzed by TEM (Transmission Electron Microscopy) and AFM (Atomic Force Microscopy).

In the absence of LPMO enzymes (FIG. 2A), it is noted that very few structures are visible on the nanometric scale.

Figure 2:
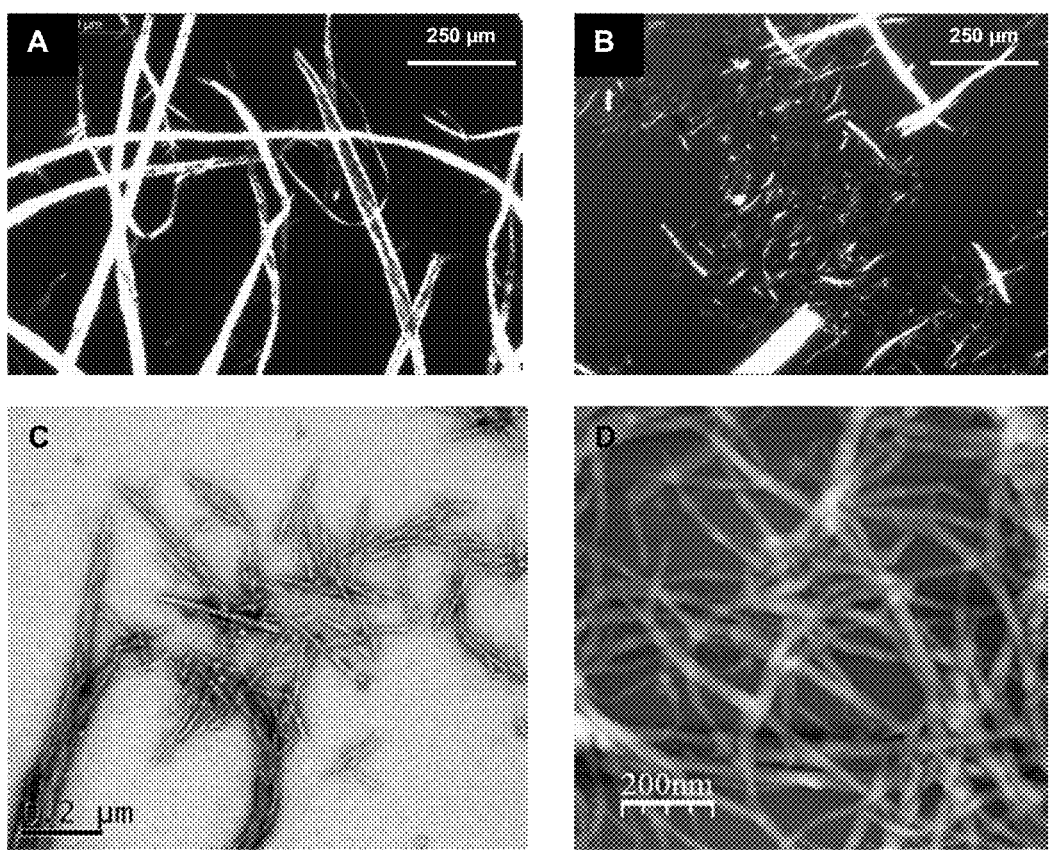
FIG. 2: Appearance of kraft fibers of cellulose that have been treated with the PaLPMO9H enzyme at an enzyme/substrate ratio of 1:50 and subjected to a weak mechanical treatment with a homogenizer-disperser of the Ultra-Turrax type and an ultrasonic treatment. Optical microscopy images of the control fibers (A) and of the treated fibers (B), and visualization of the nanofibrils obtained, by transmission electron microscopy (C) and atomic force microscopy (D).

On the other hand, for the fibers treated with the LPMO enzyme, structures of nanometric sizes are easily pinpointed, both in the supernatant and in the pellets of the experiment. The fibers are entirely destructured, allowing crystalline zones of the fiber to appear (FIG. 2C-D).

Figure 3:
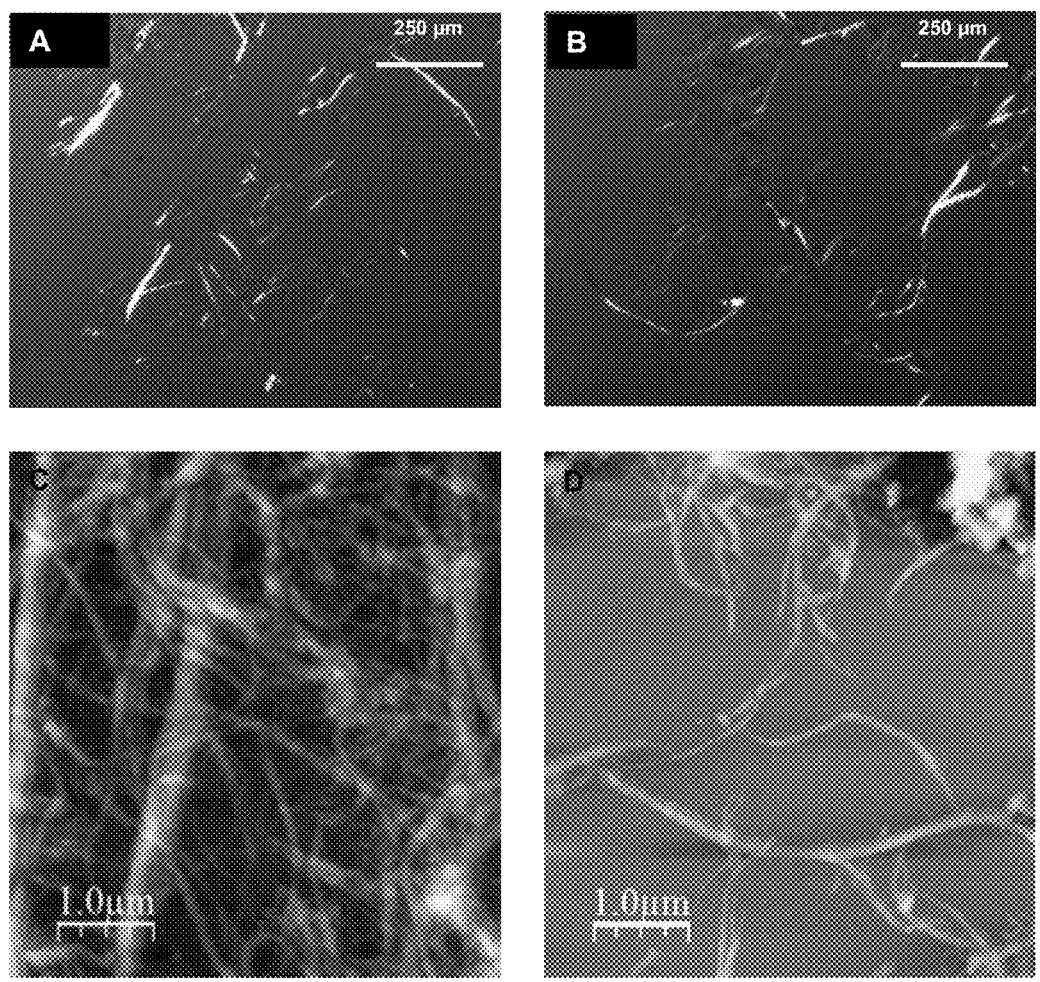
FIG. 3: Appearance of kraft fibers of cellulose that have been treated with the PaLPMO9H and PaLPMO9E enzymes according to an enzyme/substrate ratio of 1:50 and then subjected to a weak mechanical treatment with a homogenizer-disperser of the Ultra-Turrax type and an ultrasonic treatment. Optical microscopy images of the kraft fibers treated with PaLPMO9H (A) and with PaLPMO9E (B). Visualization by atomic force microscopy of the nanofibrils obtained from the kraft fibers by treatment with the LPMO enzymes PaLPMO9H (C) and PaLPMO9E (D).

The treatment of the fibers with the PaLPMO9E enzyme combined with the subsequent mechanical treatment (FIGS. 3B and D) produces a defibrillation of the cellulose that is similar to that obtained with an identical process involving the PaLPMO9H enzyme (see FIG. 3A and C).

Generally, FIGS. 2C, 2D, 3C and 3D unquestionably demonstrate that nanocelluloses are obtained.

Figure 4:
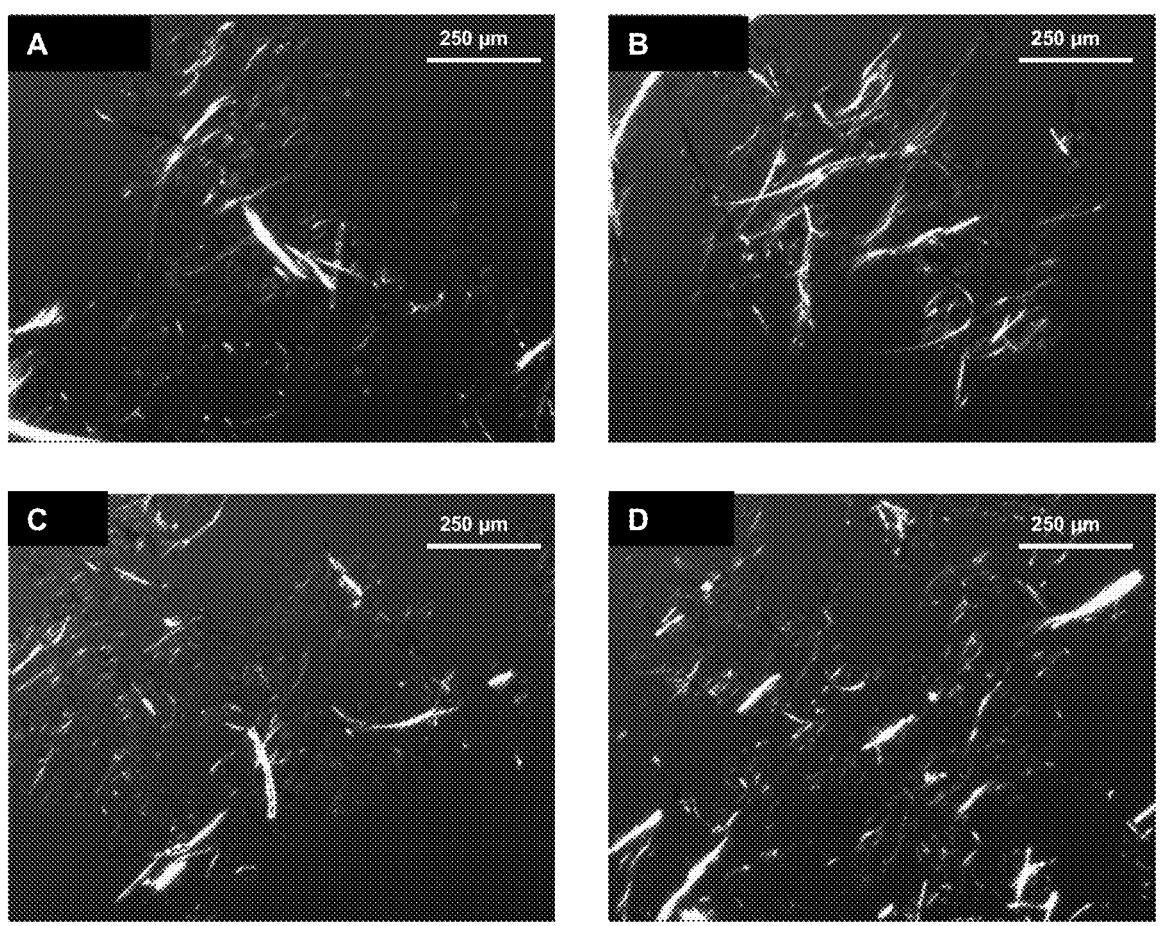
FIG. 4: Appearance of kraft fibers of cellulose that have been subjected to two successive treatments with the PaLPMO9H enzyme at various enzyme/substrate ratios and then subjected to a weak mechanical treatment with a homogenizer/disperser of the Ultra-Turrax type and an ultrasonic treatment. Optical microscopy images of the fibers treated according to the enzyme/substrate ratios of 1:50 (A); 1:100 (B); 1:500 (C) and 1:1000 (D).

If the fibers that have undergone a first treatment with the LPMO enzyme are again subjected to a second successive treatment with an LPMO enzyme under the conditions described above, followed by the mechanical treatment, the fibers are entirely destructured, including at the low enzyme/cellulose ratios (that is to say the 1/500 and 1/1000 ratios) (FIG. 4).

The AFM photos for the PaLPMO9H enzyme were analyzed using the WSxM software in order to characterize the height profile (FIG. 5A) and the size distribution (FIG. 5B) of the nanocelluloses.

This analysis shows that, at the 1:50 enzyme/cellulose ratio, the nanocelluloses have a diameter of less than 100 nm.

This result confirms that the products obtained by means of the process according to the invention are nanocelluloses.

TABLE 1

Listed fungal enzymes of the AA9 family (CAZy classification)

| Name | Organism | GenBank ref. | Uniprot ref. |
| --- | --- | --- | --- |
| Cel1 | *Agaricus bisporus* D649 | AAA53434.1 | Q00023 |
| AfA5C5.025 | *Aspergillus fumigatus* | CAF31975.1 | Q6MYM8 |
| endoglucanase/CMCase (Eng61) | *Aspergillus fumigatus* MKU1 | AFJ54163.1 | |
| endo-β-1,4-glucanase B (EgIB; AkCel61A) (Cel61A) | *Aspergillus kawachii* NBRC4308 | BAB62318.1 | Q96WQ9 |
| AN1041.2 | *Aspergillus nidulans* FGSC A4 | EAA65609.1 | C8VTW9 Q5BEI9 |
| AN3511.2 | *Aspergillus nidulans* FGSC A4 | EAA59072.1 | Q5B7G9 |
| AN9524.2 | *Aspergillus nidulans* FGSC A4 | EAA66740.1 CBF83171.1 | C8VI93 Q5AQA6 |

TABLE 1-continued

Listed fungal enzymes of the AA9 family (CAZy classification)

| Name | Organism | GenBank ref. | Uniprot ref. |
|---|---|---|---|
| AN7891.2 | *Aspergillus nidulans* FGSC A4 | EAA59545.1 | Q5AUY9 |
| AN6428.2 | *Aspergillus nidulans* FGSC A4 | EAA58450.1 | C8V0F9 Q5AZ52 |
| AN3046.2 | *Aspergillus nidulans* FGSC A4 | EAA63617.1 | C8VIS7 Q5B8T4 |
| AN3860.2 (EgIF) | *Aspergillus nidulans* FGSC A4 | EAA59125.1 | C8V6H2 Q5B6H0 |
| endo-β-1,4-glucanase (AN1602.2) | *Aspergillus nidulans* FGSC A4 | EAA64722.1 ABF50850.1 | Q5BCX8 |
| AN2388.2 | *Aspergillus nidulans* FGSC A4 | EAA64499.1 | C8VNP4 Q5BAP2 |
| An04g08550 | *Aspergillus niger* CBS 513.88 | CAK38942.1 | A2QJX0 |
| An08g05230 | *Aspergillus niger* CBS 513.88 | CAK45495.1 | A2QR94 |
| An12g02540 | *Aspergillus niger* CBS 513.88 | CAK41095.1 | A2QYU6 |
| An12g04610 | *Aspergillus niger* CBS 513.88 | CAK97151.1 | A2QZE1 |
| An14g02670 | *Aspergillus niger* CBS 513.88 | CAK46515.1 | A2R313 |
| An15g04570 | *Aspergillus niger* CBS 513.88 | CAK97324.1 | A2R5J9 |
| An15g04900 | *Aspergillus niger* CBS 513.88 | CAK42466.1 | A2R5N0 |
| AO090005000531 | *Aspergillus oryzae* RIB40 | BAE55582.1 | Q2US83 |
| AO090001000221 | *Aspergillus oryzae* RIB40 | BAE56764.1 | Q2UNV1 |
| AO090023000056 | *Aspergillus oryzae* RIB40 | BAE58643.1 | Q2UIH2 |
| AO090023000159 | *Aspergillus oryzae* RIB40 | BAE58735.1 | Q2UI80 |
| AO090023000787 | *Aspergillus oryzae* RIB40 | BAE59290.1 | Q2UGM5 |
| AO090012000090 | *Aspergillus oryzae* RIB40 | BAE60320.1 | Q2UDP5 |
| AO090138000004 | *Aspergillus oryzae* RIB40 | BAE64395.1 | Q2U220 |
| AO090103000087 | *Aspergillus oryzae* RIB40 | BAE65561.1 | Q2TYW2 |
| Cel6 (E6) | *Bipolaris maydis* C4 | AAM76663.1 | Q8J0H7 |
| glycoside hydrolase family 61 protein (Bofut4_p103280.1) | *Botryotinia fuckeliana* T4 | CCD34368.1 | |
| glycoside hydrolase family 61 protein (Bofut4_p003870.1) | *Botryotinia fuckeliana* T4 | CCD47228.1 | |
| glycoside hydrolase family 61 protein (Bofut4_p109330.1) | *Botryotinia fuckeliana* T4 | CCD48549.1 | |
| glycoside hydrolase family 61 protein (Bofut4_p025380.1) | *Botryotinia fuckeliana* T4 | CCD50139.1 | |
| glycoside hydrolase family 61 protein (Bofut4_p025430.1) | *Botryotinia fuckeliana* T4 | CCD50144.1 | |
| glycoside hydrolase family 61 protein (Bofut4_p018100.1) | *Botryotinia fuckeliana* T4 | CCD51504.1 | |
| glycoside hydrolase family 61 protein (Bofut4_p031660.1) | *Botryotinia fuckeliana* T4 | CCD49290.1 | |
| glycoside hydrolase family 61 protein (Bofut4_p000920.1) | *Botryotinia fuckeliana* T4 | CCD52645.1 | |
| BofuT4P143000045001 | *Botryotinia fuckeliana* T4 | CCD50451.2 CCD50451.1 | |
| ORF | *Chaetomium thermophilum* CT2 | AGY80102.1 | |
| ORF (fragment) | *Chaetomium thermophilum* CT2 | AGY80103.1 | |
| ORF (fragment) | *Chaetomium thermophilum* CT2 | AGY80104.1 | |
| ORF (fragment) | *Chaetomium thermophilum* CT2 | AGY80105.1 | |
| cellobiohydrolase family protein 61, partial (Cbh61-2) (fragment) | *Chaetomium thermophilum* CT2 | AGY80103.1 | |
| cellobiohydrolase family protein 61, partial (Cbh61-3) (fragment) | *Chaetomium thermophilum* CT2 | AGY80104.1 | |
| cellobiohydrolase family protein 61, partial (Cbh61-4) (fragment) | *Chaetomium thermophilum* CT2 | AGY80105.1 | |

TABLE 1-continued

Listed fungal enzymes of the AA9 family (CAZy classification)

| Name | Organism | GenBank ref. | Uniprot ref. |
| --- | --- | --- | --- |
| ORF (possible fragment) | *Colletotrichum graminicola* M2 | CAQ16278.1 | B5WYD8 |
| ORF | *Colletotrichum graminicola* M2 | CAQ16206.1 | B5WY66 |
| ORF | *Colletotrichum graminicola* M2 | CAQ16208.1 | B5WY68 |
| ORF | *Colletotrichum graminicola* M2 | CAQ16217.1 | B5WY77 |
| unnamed protein product | *Coprinopsis cinerea* | CAG27578.1 | |
| CGB_A6300C | *Cryptococcus bacillisporus* WM276 | ADV19810.1 | |
| CNAG_00601 | *Cryptococcus neoformans* var. *grubii* H99 (Cryne_H99_1) | AFR92731.1 AFR92731.2 | |
| Cel1 | *Cryptococcus neoformans* var. *neoformans* | AAC39449.1 | O59899 |
| CNA05840 (Cel1) | *Cryptococcus neoformans* var. *neoformans* JEC21 (Cryne_JEC21_1) | AAW41121.1 | F5HH24 |
| ORF (fragment) | *Flammulina velutipes* KACC 42777 | ADX07320.1 | |
| FFUJ_12340 | *Fusarium fujikuroi* IMI 58289 (Fusfu1) | CCT72465.1 | |
| FFUJ_13305 | *Fusarium fujikuroi* IMI 58289 (Fusfu1) | CCT67119.1 | |
| FFUJ_07829 | *Fusarium fujikuroi* IMI 58289 (Fusfu1) | CCT69268.1 | |
| FFUJ_12621 | *Fusarium fujikuroi* IMI 58289 (Fusfu1) | CCT72729.1 | |
| FFUJ_12840 | *Fusarium fujikuroi* IMI 58289 (Fusfu1) | CCT72942.1 | |
| FFUJ_09373 | *Fusarium fujikuroi* IMI 58289 (Fusfu1) | CCT73805.1 | |
| FFUJ_10599 | *Fusarium fujikuroi* IMI 58289 (Fusfu1) | CCT74544.1 | |
| FFUJ_10643 | *Fusarium fujikuroi* IMI 58289 (Fusfu1) | CCT74587.1 | |
| FFUJ_14514 | *Fusarium fujikuroi* IMI 58289 (Fusfu1) | CCT67584.1 | |
| FFUJ_11399 | *Fusarium fujikuroi* IMI 58289 (Fusfu1) | CCT75380.1 | |
| FFUJ_14514 | *Fusarium fujikuroi* IMI 58289 | CCT67584.1 | |
| FFUJ_11399 | *Fusarium fujikuroi* IMI 58289 | CCT75380.1 | |
| FFUJ_04652 | *Fusarium fujikuroi* IMI 58289 (Fusfu1) | CCT64153.1 | |
| FFUJ_03777 | *Fusarium fujikuroi* IMI 58289 (Fusfu1) | CCT64954.1 | |
| FFUJ_04940 | *Fusarium fujikuroi* IMI 58289 (Fusfu1) | CCT63889.1 | |
| Sequence 122805 from patent U.S. Pat. No. 7,214,786 | *Fusarium graminearum* | ABT35335.1 | |
| FG03695.1 (Cel61E) | *Fusarium graminearum* PH-1 | XP_383871.1 | |
| unnamed protein product | *Fusarium graminearum* PH-1 | CEF78545.1 | |
| unnamed protein product | *Fusarium graminearum* PH-1 | CEF74901.1 | |
| unnamed protein product | *Fusarium graminearum* PH-1 | CEF78472.1 | |
| unnamed protein product | *Fusarium graminearum* PH-1 | CEF86346.1 | |
| unnamed protein product | *Fusarium graminearum* PH-1 | CEF87450.1 | |
| unnamed protein product | *Fusarium graminearum* PH-1 | CEF85876.1 | |
| unnamed protein product | *Fusarium graminearum* PH-1 | CEF86254.1 | |

TABLE 1-continued

Listed fungal enzymes of the AA9 family (CAZy classification)

| Name | Organism | GenBank ref. | Uniprot ref. |
|---|---|---|---|
| unnamed protein product | *Fusarium graminearum* PH-1 | CEF87657.1 | |
| unnamed protein product | *Fusarium graminearum* PH-1 | CEF76256.1 | |
| unnamed protein product | *Fusarium graminearum* PH-1 | CEF78876.1 | |
| unnamed protein product | *Fusarium graminearum* PH-1 | CEF79735.1 | |
| unnamed protein product | *Fusarium graminearum* PH-1 | CEF74460.1 | |
| unnamed protein product | *Fusarium graminearum* PH-1 | CEF84640.1 | |
| endo-β-1,4-glucanase (Cel61G) | *Gloeophyllum trabeum* | AEJ35168.1 | |
| GH61D | *Heterobasidion parviporum* | AFO72234.1 | |
| GH61B | *Heterobasidion parviporum* | AFO72233.1 | |
| GH61A | *Heterobasidion parviporum* | AFO72232.1 | |
| GH61F | *Heterobasidion parviporum* | AFO72235.1 | |
| GH61G | *Heterobasidion parviporum* | AFO72236.1 | |
| GH61H | *Heterobasidion parviporum* | AFO72237.1 | |
| GH61I | *Heterobasidion parviporum* | AFO72238.1 | |
| GH61J | *Heterobasidion parviporum* | AFO72239.1 | |
| unnamed protein product | *Humicola insolens* | CAG27577.1 | |
| endoglucanase IV (EgiV) | *Hypocrea orientalis* EU7-22 | AFD50197.1 | |
| GH61A (GH61A) | *Lasiodiplodia theobromae* CBS 247.96 | CAJ81215.1 | |
| GH61B (GH61B) | *Lasiodiplodia theobromae* CBS 247.96 | CAJ81216.1 | |
| GH61C (GH61C) | *Lasiodiplodia theobromae* CBS 247.96 | CAJ81217.1 | |
| GH61D (GH61D) | *Lasiodiplodia theobromae* CBS 247.96 | CAJ81218.1 | |
| ORF | *Leptosphaeria maculans* v23.1.3 | CBX91313.1 | E4ZJM8 |
| ORF | *Leptosphaeria maculans* v23.1.3 | CBX93546.1 | E4ZQ11 |
| ORF | *Leptosphaeria maculans* v23.1.3 | CBX94224.1 | E4ZS44 |
| ORF | *Leptosphaeria maculans* v23.1.3 | CBX94532.1 | E4ZSU4 |
| ORF | *Leptosphaeria maculans* v23.1.3 | CBX94572.1 | E4ZSY4 |
| ORF | *Leptosphaeria maculans* v23.1.3 | CBX95655.1 | E4ZVM9 |
| ORF | *Leptosphaeria maculans* v23.1.3 | CBX96476.1 | E4ZZ41 |
| ORF | *Leptosphaeria maculans* v23.1.3 | CBX96550.1 | E4ZYM4 |
| ORF | *Leptosphaeria maculans* v23.1.3 | CBX96949.1 | E5A089 |
| ORF | *Leptosphaeria maculans* v23.1.3 | CBX97718.1 | E5A201 |
| ORF | *Leptosphaeria maculans* v23.1.3 | CBX98126.1 | E5A3B3 |
| ORF | *Leptosphaeria maculans* v23.1.3 | CBY01974.1 | E5AFI5 |
| ORF | *Leptosphaeria maculans* v23.1.3 | CBY02242.1 | E5ACP0 |
| ORF | *Leptosphaeria maculans* v23.1.3 | CBX91667.1 | E4ZK72 |
| ORF | *Leptosphaeria maculans* v23.1.3 | CBX93965.1 | E4ZQA3 |

TABLE 1-continued

Listed fungal enzymes of the AA9 family (CAZy classification)

| Name | Organism | GenBank ref. | Uniprot ref. |
| --- | --- | --- | --- |
| ORF | *Leptosphaeria maculans* v23.1.3 | CBX98254.1 | E5A3P1 |
| ORF (fragment) | *Leptosphaeria maculans* v23.1.3 | CBY00196.1 | E5A955 |
| ORF | *Leptosphaeria maculans* v23.1.3 | CBY01204.1 | E5AC13 |
| predicted protein (Lema_p000430.1) (fragment) | *Leptosphaeria maculans* v23.1.3 | CBY01256.1 | E5ADG7 |
| ORF (fragment) | *Leptosphaeria maculans* v23.1.3 | CBY01257.1 | E5ADG8 |
| lytic polysaccharide monooxygenase | *Leucoagaricus gongylophorus* Ae322 | CDJ79823.1 | |
| MG05364.4 | *Magnaporthe grisea* 70-15 (Maggr1) | EAA54572.1 XP_359989.1 | |
| MG07686.4 | *Magnaporthe grisea* 70-15 (Maggr1) | EAA53409.1 XP_367775.1 | G4N3E5 |
| MG07300.4 | *Magnaporthe grisea* 70-15 (Maggr1) | EAA56945.1 XP_367375.1 | G4MUY8 |
| MG08020.4 | *Magnaporthe grisea* 70-15 (Maggr1) | EAA57051.1 XP_362437.1 | |
| MG08254.4 | *Magnaporthe grisea* 70-15 (Maggr1) | EAA57285.1 XP_362794.1 | G4MXC7 |
| MG08066.4 (fragment) | *Magnaporthe grisea* 70-15 (Maggr1) | EAA57097.1 XP_362483.1 | G4MXS5 |
| MG04547.4 | *Magnaporthe grisea* 70-15 (Maggr1) | EAA50788.1 XP_362102.1 | G4MS66 |
| MG08409.4 | *Magnaporthe grisea* 70-15 (Maggr1) | EAA57439.1 XP_362640.1 | G4MVX4 |
| MG09709.4 | *Magnaporthe grisea* 70-15 (Maggr1) | EAA49718.1 XP_364864.1 | G4NAI5 |
| MG06069.4 | *Magnaporthe grisea* 70-15 (Maggr1) | EAA52941.1 XP_369395.1 | G4N560 |
| MG09439.4 | *Magnaporthe grisea* 70-15 (Maggr1) | EAA51422.1 XP_364487.1 | G4NHT8 |
| MG06229.4 | *Magnaporthe grisea* 70-15 (Maggr1) | EAA56258.1 XP_369714.1 | |
| MG07631.4 | *Magnaporthe grisea* 70-15 (Maggr1) | EAA53354.1 XP_367720.1 | G4N2Z0 |
| MGG_06621 | *Magnaporthe grisea* 70-15 (Maggr1) | XP_003716906.1 XP_370106.1 | |
| MGG_12696 | *Magnaporthe grisea* 70-15 (Maggr1) | XP_003721313.1 | |
| MGG_02502 | *Magnaporthe grisea* 70-15 (Maggr1) | XP_003709306.1 EAA54517.1 XP_365800.1 | |
| MGG_04057 | *Magnaporthe grisea* 70-15 (Maggr1) | XP_003719782.1 EAA50298.1 XP_361583.1 | |
| MGG_13241 | *Magnaporthe grisea* 70-15 (Maggr1) | XP_003711808.1 | |
| MGG_13622 | *Magnaporthe grisea* 70-15 (Maggr1) | XP_003717521.1 | |
| MGG_07575 | *Magnaporthe grisea* 70-15 (Maggr1) | XP_003711490.1 EAA53298.1 XP_367664.1 | |
| MGG_11948 | *Magnaporthe grisea* 70-15 (Maggr1) | XP_003709110.1 | |

TABLE 1-continued

Listed fungal enzymes of the AA9 family (CAZy classification)

| Name | Organism | GenBank ref. | Uniprot ref. |
| --- | --- | --- | --- |
| MGG_16080 (fragment) | *Magnaporthe grisea* 70-15 (Maggr1) | XP_003709033.1 | |
| MGG_16043 (fragment) | *Magnaporthe grisea* 70-15 (Maggr1) | XP_003708922.1 | |
| MGG_12733 (probable fragment) | *Magnaporthe grisea* 70-15 (Maggr1) | XP_003716689.1 | |
| copper-dependent polysaccharide monooxygenases (Gh61) (fragment) | *Malbranchea cinnamomea* CBS 115.68 | CCP37674.1 | |
| copper-dependent polysaccharide monooxygenases (Gh61) (fragment) | *Melanocarpus albomyces* CBS 638.94 | CCP37668.1 | |
| copper-dependent polysaccharide monooxygenases (Gh61) (fragment) | *Myceliophthora fergusii* CBS 406.69 | CCP37667.1 | |
| MYCTH_2112799 | *Myceliophthora thermophila* ATCC 42464 | AEO61257.1 | |
| MYCTH_79765 | *Myceliophthora thermophila* ATCC 42464 | AEO56016.1 | |
| MYCTH_110651 | *Myceliophthora thermophila* ATCC 42464 | AEO54509.1 | |
| MYCTH_2298502 | *Myceliophthora thermophila* ATCC 42464 | AEO55082.1 | |
| MYCTH_2299721 | *Myceliophthora thermophila* ATCC 42464 | AEO55652.1 | |
| MYCTH_2054500 | *Myceliophthora thermophila* ATCC 42464 | AEO55776.1 | |
| MYCTH_111088 | *Myceliophthora thermophila* ATCC 42464 | AEO56416.1 | |
| β-glycan-cleaving enzyme (StCel61a; MYCTH_46583) (Cel61A) | *Myceliophthora thermophila* ATCC 42464 | AEO56542.1 | |
| MYCTH_2301632 | *Myceliophthora thermophila* ATCC 42464 | AEO56547.1 | |
| MYCTH_100518 | *Myceliophthora thermophila* ATCC 42464 | AEO56642.1 | |
| lytic polysaccharide monooxygenases (active on cellulose) (MYCTH_92668) | *Myceliophthora thermophila* ATCC 42464 | AEO56665.1 | |
| MYCTH_2060403 | *Myceliophthora thermophila* ATCC 42464 | AEO58412.1 | |
| MYCTH_2306673 | *Myceliophthora thermophila* ATCC 42464 | AEO58921.1 | |
| MYCTH_116175 (fragment) | *Myceliophthora thermophila* ATCC 42464 | AEO59482.1 | |
| MYCTH_96032 | *Myceliophthora thermophila* ATCC 42464 | AEO59823.1 | |
| MYCTH_103537 | *Myceliophthora thermophila* ATCC 42464 | AEO59836.1 | |
| MYCTH_55803 | *Myceliophthora thermophila* ATCC 42464 | AEO59955.1 | |
| lytic polysaccharide monooxygenases (active on cellulose) (MYCTH_112089) | *Myceliophthora thermophila* ATCC 42464 | AEO60271.1 | |
| MYCTH_85556 | *Myceliophthora thermophila* ATCC 42464 | AEO61304.1 | |

TABLE 1-continued

Listed fungal enzymes of the AA9 family (CAZy classification)

| Name | Organism | GenBank ref. | Uniprot ref. |
|---|---|---|---|
| MYCTH_2311323 | *Myceliophthora thermophila* ATCC 42464 | AEO61305.1 | |
| MYCTH_47093 (fragment) | *Myceliophthora thermophila* ATCC 42464 | AEO56498.1 | |
| MYCTH_80312 | *Myceliophthora thermophila* ATCC 42464 | AEO58169.1 | |
| lytic polysaccharide monooxygenase (active on cellulose) (PMO-2; NcLPMO9D; GH61-4; NCU01050) (LPMO9D) | *Neurospora crassa* OR74A | CAD21296.1 EAA32426.1 XP_326543.1 | Q1K8B6 Q8WZQ2 |
| lytic polysaccharide monooxygenase (active on cellulose) (PMO-03328; NcLPMO9F; GH61-6; NCU03328) (LPMO9F) | *Neurospora crassa* OR74A | CAD70347.1 EAA26656.1 XP_322586.1 | Q1K4Q1 Q873G1 |
| lytic polysaccharide monooxygenase (PMO-01867; NcLPMO9J; GH61-10; NCU01867; B13N4.070) (LPMO9J) | *Neurospora crassa* OR74A | CAE81966.1 EAA36262.1 XP_329057.1 | Q7SHD9 |
| NCU02344.1 (B23N11.050) | *Neurospora crassa* OR74A | CAF05857.1 EAA30230.1 XP_331120.1 | Q7S411 |
| lytic polysaccharide monooxygenase (active on cellulose) (PMO-3; NcLPMO9M; GH61-13; NcPMO-3; NCU07898) (LPMO9M) | *Neurospora crassa* OR74A | EAA33178.1 XP_328604.1 | Q7SA19 |
| NCU05969.1 | *Neurospora crassa* OR74A | EAA29347.1 XP_325824.1 | Q7S1V2 |
| lytic polysaccharide monooxygenase (active on cellulose and cellooligosaccharides) (PMO-02916; NcLPMO9C; GH61-3; NCU02916) (LPMO9C) | *Neurospora crassa* OR74A | EAA36362.1 XP_330104.1 | Q7SHI8 |
| lytic polysaccharide monooxygenase (active on cellulose) (GH61-2; NCU07760) | *Neurospora crassa* OR74A | EAA29018.1 XP_328466.1 | Q7S1I1 |
| NCU07520.1 | *Neurospora crassa* OR74A | EAA29132.1 XP_327806.1 | Q7S1A0 |
| lytic polysaccharide monooxygenase (active on cellulose) (GH61-1; NCU02240) | *Neurospora crassa* OR74A | EAA30263.1 XP_331016.1 | Q7S439 |
| lytic polysaccharide monooxygenase (active on cellulose) (NCU00836) | *Neurospora crassa* OR74A | EAA34466.1 XP_325016.1 | Q7SCJ5 |
| lytic polysaccharide monooxygenase (active on cellulose) (PMO-08760; NcLPMO9E; GH61-5; NCU08760) (LPMO9E) | *Neurospora crassa* OR74A | EAA26873.1 XP_330877.1 | Q7RWN7 |
| NCU07974.1 | *Neurospora crassa* OR74A | EAA33408.1 XP_328680.1 | Q7SAR4 |
| NCU03000.1 (B24P7.180) | *Neurospora crassa* OR74A | EAA36150.1 CAB97283.2 XP_330187.1 | Q7RV41 Q9P3R7 |
| cellulose monooxygenase | *Penicillium oxalicum* GZ-2 | AIO06742.1 | |
| Pc12g13610 | *Penicillium chrysogenum* Wisconsin 54-1255 (PenchWisc1_1) | CAP80988.1 | B6H0I6 |
| Pc13g07400 | *Penicillium chrysogenum* Wisconsin 54-1255 (PenchWisc1_1) | CAP91809.1 | B6H3U0 |
| Pc13g13110 | *Penicillium chrysogenum* Wisconsin 54-1255 (PenchWisc1_1) | CAP92380.1 | B6H3A3 |

TABLE 1-continued

Listed fungal enzymes of the AA9 family (CAZy classification)

| Name | Organism | GenBank ref. | Uniprot ref. |
|---|---|---|---|
| Pc20g11100 | *Penicillium chrysogenum* Wisconsin 54-1255 (PenchWisc1_1) | CAP86439.1 | B6HG02 |
| Cel61 (Cel61A) | *Phanerochaete chrysosporium* BKM-F-1767 | AAM22493.1 | Q8NJI9 |
| Lytic polysaccharide mono-oxygenase active on cellulose (Gh61D; PcGH61D) | *Phanerochaete chrysosporium* K-3 | BAL43430.1 | |
| PIIN_01487 | *Piriformospora indica* (Pirin1) | CCA67659.1 | |
| PIIN_02110 | *Piriformospora indica* (Pirin1) | CCA68244.1 | |
| PIIN_03975 | *Piriformospora indica* (Pirin1) | CCA70035.1 | |
| PIIN_04357 | *Piriformospora indica* (Pirin1) | CCA70418.1 | |
| PIIN_04637 | *Piriformospora indica* (Pirin1) | CCA70703.1 | |
| PIIN_06117 | *Piriformospora indica* (Pirin1) | CCA72182.1 | |
| PIIN_06118 | *Piriformospora indica* (Pirin1) | CCA72183.1 | |
| PIIN_06127 | *Piriformospora indica* (Pirin1) | CCA72192.1 | |
| PIIN_06155 | *Piriformospora indica* (Pirin1) | CCA72220.1 | |
| PIIN_07098 | *Piriformospora indica* (Pirin1) | CCA73144.1 | |
| PIIN_07105 | *Piriformospora indica* (Pirin1) | CCA73151.1 | |
| PIIN_08199 | *Piriformospora indica* (Pirin1) | CCA74246.1 | |
| PIIN_08783 | *Piriformospora indica* (Pirin1) | CCA74814.1 | |
| PIIN_09022 | *Piriformospora indica* (Pirin1) | CCA75037.1 | |
| PIIN_00566 (fragment) | *Piriformospora indica* (Pirin1) | CCA66803.1 | |
| PIIN_01484 | *Piriformospora indica* (Pirin1) | CCA67656.1 | |
| PIIN_01485 (fragment) | *Piriformospora indica* (Pirin1) | CCA67657.1 | |
| PIIN_01486 (fragment) | *Piriformospora indica* (Pirin1) | CCA67658.1 | |
| PIIN_04356 | *Piriformospora indica* (Pirin1) | CCA70417.1 | |
| PIIN_05699 (fragment) | *Piriformospora indica* (Pirin1) | CCA71764.1 | |
| PIIN_06156 | *Piriformospora indica* (Pirin1) | CCA72221.1 | |
| PIIN_08402 | *Piriformospora indica* (Pirin1) | CCA74449.1 | |
| PIIN_10315 (fragment) | *Piriformospora indica* (Pirin1) | CCA76320.1 | |
| PIIN_10660 (fragment) | *Piriformospora indica* (Pirin1) | CCA76671.1 | |
| PIIN_00523 (fragment) | *Piriformospora indica* (Pirin1) | CCA77877.1 | |
| Putative Glycoside Hydrolase Family 61 | *Podospora anserina* S mat+ (Podan2) | CDP30131.1 CAP64732.1 | B2AL94 |
| Putative Glycoside Hydrolase Family 61 | *Podospora anserina* S mat+ (Podan2) | CDP30928.1 CAP71532.1 | B2B346 |
| Pa_1_500 | *Podospora anserina* S mat+ (Podan2) | CAP59702.1 CDP22345.1 | B2A9F5 |
| Pa_4_350 | *Podospora anserina* S mat+ (Podan2) | CAP61395.1 CDP27750.1 | B2AD80 |
| Pa_4_1020 | *Podospora anserina* S mat+ (Podan2) | CAP61476.1 CDP27830.1 | B2ADG1 |

TABLE 1-continued

Listed fungal enzymes of the AA9 family (CAZy classification)

| Name | Organism | GenBank ref. | Uniprot ref. |
|---|---|---|---|
| Pa_0_270 | Podospora anserina S mat+ (Podan2) | CAP61650.1 CDP28001.1 | B2ADY5 |
| Pa_5_8940 | Podospora anserina S mat+ (Podan2) | CAP64619.1 CDP30017.1 | B2AKU6 |
| Pa_5_4100 (fragment) | Podospora anserina S mat+ (Podan2) | CAP64865.1 CDP29378.1 | B2ALM7 |
| Pa_5_6950 | Podospora anserina S mat+ (Podan2) | CAP65111.1 CDP29800.1 | B2AMI8 |
| Pa_5_10660 | Podospora anserina S mat+ (Podan2) | CAP65855.1 CDP30283.1 | B2APD8 |
| Pa_5_10760 | Podospora anserina S mat+ (Podan2) | CAP65866.1 CDP30272.1 | B2APE9 |
| Pa_5_11630 (fragment) | Podospora anserina S mat+ (Podan2) | CAP65971.1 CDP30166.1 | B2API9 |
| Pa_4_7570 | Podospora anserina S mat+ (Podan2) | CAP66744.1 CDP28479.1 | B2ARG6 |
| Pa_1_21900 (fragment) | Podospora anserina S mat+ (Podan2) | CAP67176.1 CDP24589.1 | B2AS05 |
| Pa_1_22040 | Podospora anserina S mat+ (Podan2) | CAP67190.1 CDP24603.1 | B2AS19 |
| Pa_1_22150 (fragment) | Podospora anserina S mat+ (Podan2) | CAP67201.1 CDP24614.1 | B2AS30 |
| Pa_6_11220 | Podospora anserina S mat+ (Podan2) | CAP67466.1 CDP30332.1 | B2ASU3 |
| Pa_6_11370 | Podospora anserina S mat+ (Podan2) | CAP67481.1 CDP30347.1 | B2ASV8 |
| Pa_6_11470 | Podospora anserina S mat+ (Podan2) | CAP67493.1 CDP30359.1 | B2ASX0 |
| Pa_1_16300 | Podospora anserina S mat+ (Podan2) | CAP67740.1 CDP23998.1 | B2ATL7 |
| Pa_7_5030 | Podospora anserina S mat+ (Podan2) | CAP68173.1 CDP31642.1 | B2AUV0 |
| Pa_7_3770 | Podospora anserina S mat+ (Podan2) | CAP68309.1 CDP31780.1 | B2AV86 |
| Pa_7_3390 | Podospora anserina S mat+ (Podan2) | CAP68352.1 CDP31823.1 | B2AVC8 |
| lytic polysaccharide mono-oxygenase active on cellulose (Gh61B; Pa_7_3160)(Gh61B) | Podospora anserina S mat+ (Podan2) | CAP68375.1 CDP31846.1 | B2AVF1 |
| Pa_6_7780 | Podospora anserina S mat+ (Podan2) | CAP71839.1 CDP31230.1 | B2B403 |
| Pa_2_1700 | Podospora anserina S mat+ (Podan2) | CAP72740.1 CDP25137.1 | B2B4L5 |
| Pa_2_4860 | Podospora anserina S mat+ (Podan2) | CAP73072.1 CDP25472.1 | B2B5J7 |
| lytic polysaccharide mono-oxygenase active on cellulose (Gh61A; Pa_2_6530)(Gh61A) | Podospora anserina S mat+ (Podan2) | CAP73254.1 CDP25655.1 | B2B629 |
| Pa_2_7040 | Podospora anserina S mat+ (Podan2) | CAP73311.1 CDP25714.1 | B2B686 |
| Pa_2_7120 | Podospora anserina S mat+ (Podan2) | CAP73320.1 CDP25723.1 | B2B695 |

TABLE 1-continued

Listed fungal enzymes of the AA9 family (CAZy classification)

| Name | Organism | GenBank ref. | Uniprot ref. |
|---|---|---|---|
| Pa_3_190 | *Podospora anserina* S mat+ (Podan2) | CAP61048.1 CDP26500.1 | B2AC83 |
| Pa_3_2580 | *Podospora anserina* S mat+ (Podan2) | CAP70156.1 CDP26748.1 | B2AZV6 |
| Pa_3_3310 | *Podospora anserina* S mat+ (Podan2) | CAP70248.1 CDP26841.1 | B2AZD4 |
| endo-β-1,4-glucanase (Egl1; PIEGL1) | *Pyrenochaeta lycopersici* ISPaVe ER 1211 | AEV53599.1 | |
| copper-dependent polysaccharide monooxygenases (Gh61) (fragment) | *Rasamsonia byssochlamydoides* CBS 151.75 | CCP37669.1 | |
| copper-dependent polysaccharide monooxygenases (Gh61) (fragment) | *Remersonia thermophila* CBS 540.69 | CCP37675.1 | |
| RHTO0S_28e01816g | *Rhodosporidium toruloides* CECT1137 | CDR49619.1 | |
| copper-dependent polysaccharide monooxygenases (Gh61) (fragment) | *Scytalidium indonesiacum* CBS 259.81 | CCP37676.1 | |
| SMU2916 (fragment) | *Sordaria macrospora* k-hell | CAQ58424.1 | C1KU36 |
| lytic polysaccharide mono-oxygenase active on cellulose | *Thermoascus aurantiacus* | ABW56451.1 ACS05720.1 | |
| copper-dependent polysaccharide monooxygenases (Gh61) (fragment) | *Thermoascus aurantiacus* CBS 891.70 | CCP37673.1 | |
| ORF | *Thermoascus aurantiacus* var. *levisporus* | AGO68294.1 | |
| copper-dependent polysaccharide monooxygenases (Gh61) (fragment) | *Thermomyces dupontii* CBS 236.58 | CCP37672.1 | |
| copper-dependent polysaccharide monooxygenases (Gh61) (fragment) | *Thermomyces lanuginosus* CBS 632.91 | CCP37678.1 | |
| unnamed protein product | *Thielavia terrestris* | CAG27576.1 | |
| THITE_2106556 | *Thielavia terrestris* NRRL 8126 | AEO62422.1 | |
| THITE_2116536 | *Thielavia terrestris* NRRL 8126 | AEO67662.1 | |
| THITE_2040127 | *Thielavia terrestris* NRRL 8126 | AEO64605.1 | |
| THITE_2119040 | *Thielavia terrestris* NRRL 8126 | AEO69044.1 | |
| THITE_115795 | *Thielavia terrestris* NRRL 8126 | AEO64177.1 | |
| THITE_2110890 | *Thielavia terrestris* NRRL 8126 | AEO64593.1 | |
| THITE_2112626 | *Thielavia terrestris* NRRL 8126 | AEO65532.1 | |
| THITE_2076863 | *Thielavia terrestris* NRRL 8126 | AEO65580.1 | |
| THITE_170174 | *Thielavia terrestris* NRRL 8126 | AEO66274.1 | |
| THITE_2044372 | *Thielavia terrestris* NRRL 8126 | AEO67396.1 | |
| THITE_2170662 | *Thielavia terrestris* NRRL 8126 | AEO68023.1 | |
| THITE_128130 | *Thielavia terrestris* NRRL 8126 | AEO68157.1 | |
| THITE_2145386 | *Thielavia terrestris* NRRL 8126 | AEO68577.1 | |
| THITE_2054543 | *Thielavia terrestris* NRRL 8126 | AEO68763.1 | |
| THITE_2059487 | *Thielavia terrestris* NRRL 8126 | AEO71031.1 | |
| THITE_2142696 | *Thielavia terrestris* NRRL 8126 | AEO67395.1 | |
| THITE_43665 | *Thielavia terrestris* NRRL 8126 | AEO69043.1 | |

TABLE 1-continued

Listed fungal enzymes of the AA9 family (CAZy classification)

| Name | Organism | GenBank ref. | Uniprot ref. |
| --- | --- | --- | --- |
| THITE_2085430 (fragment) | *Thielavia terrestris* NRRL 8126 | AEO63926.1 | |
| THITE_2122979 | *Thielavia terrestris* NRRL 8126 | XP_003657366.1 | |
| cellulase-enhancing factor (GH61B) | *Thielavia terrestris* NRRL 8126 | ACE10231.1 | |
| Sequence 4 from patent U.S. Pat. No. 7,361,495 (GH61C) | *Thielavia terrestris* NRRL 8126 | ACE10232.1 | |
| Sequence 4 from patent U.S. Pat. No. 7,361,495 (GH61C) | *Thielavia terrestris* NRRL 8126 | ACE10232.1 | |
| Sequence 6 from patent U.S. Pat. No. 7,361,495 (GH61D) | *Thielavia terrestris* NRRL 8126 | ACE10233.1 | |
| Sequence 6 from patent U.S. Pat. No. 7,361,495 (GH61D) | *Thielavia terrestris* NRRL 8126 | ACE10233.1 | |
| lytic polysaccharide mono-oxygenase active on cellulose (131562; TtGH61E)(GH61E) | *Thielavia terrestris* NRRL 8126 | AEO71030.1 ACE10234.1 | |
| Sequence 10 from patent U.S. Pat. No. 7,361,495 (GH61G) | *Thielavia terrestris* NRRL 8126 | ACE10235.1 | |
| Sequence 10 from patent U.S. Pat. No. 7,361,495 (GH61G) | *Thielavia terrestris* NRRL 8126 | ACE10235.1 | |
| Lytic polysaccharide mono-oxygenase active on cellulose (EG7; HjGH61B)(Cel61B = GH61B) | *Trichoderma reesei* QM6A | AAP57753.1 ABH82048.1 ACK19226.1 ACR92640.1 | Q7Z9M7 |
| endo-γ-1,4-glucanase IV (EGIV; Egl4; EG4) (Cel61A) | *Trichoderma reesei* RUTC-30 | CAA71999.1 | O14405 |
| endoglucanase (EnGluIV; EndoGluIV) | *Trichoderma saturnisporum* | ADB89217.1 | D3JTC4 |
| endoglucanase IV (EgIV; EG IV) | *Trichoderma* sp. SSL | ACH92573.1 | B5TYI4 |
| endoglucanase VII (EgvII) | *Trichoderma viride* AS 3.3711 | ACD36971.1 | B4YEW1 |
| endoglucanase IV (EgIV) | *Trichoderma viride* AS 3.3711 | ADJ57703.1 ACD36973.1 | B4YEW3 D9IXC6 |
| AAA12YM05FL | uncultured eukaryote | CCA94933.1 | |
| AAA2YG01FL | uncultured eukaryote | CCA94930.1 | |
| AAA15YI10FL | uncultured eukaryote | CCA94931.1 | |
| AAA21YH11FL | uncultured eukaryote | CCA94932.1 | |
| ABA3YP05FL | uncultured eukaryote | CCA94934.1 | |
| endoglucanase II (EgII) | *Volvariella volvacea* | AFP23133.1 | |
| endoglucanase II (EgII) | *Volvariella volvacea* V14 | AAT64005.1 | Q6E5B4 |
| Unknown | *Zea mays* B73 | ACF86151.1 | |
| unknown (ZM_BFc0036G02) | *Zea mays* B73 | ACF78974.1 ACR36748.1 | B4FA31 |

TABLE 2

LPMOs (AA9, AA10 and AA11 families of the CAZy classification)

| Organism | Uniprot ref. | GenBank ref. | Other names | Substrate specificity | Known selectivity | Modularity |
| --- | --- | --- | --- | --- | --- | --- |
| fungi | | | | | | |
| *A. oryzae* | Q2UA85 | BAE61530 | AoAA11 | chitin | C1 | AA11-X278 |
| *A. nidulans* | C8VGF8 | EAA62623.1 | AnAA13 | starch | C1 | AA13-CBM20 |
| *M. thermophila* | G2QI82 | AEO60271 | MYCTH_112089 | cellulose | C1 | AA9 |
| *M. thermophila* | G2QAB5 | AEO56665 | MYCTH_92668 | cellulose | C1 | AA9 |
| *N. crassa* | Q7RWN7 | EAA26873 | NcLPMO9E | cellulose | C1 | AA9-CBM1 |
| *N. crassa* | Q1K8B6 Q8WZQ2 | EAA32426 CAD21296 | NcLPMO9D | cellulose | C4 | AA9 |
| *N. crassa* | Q7SA19 | EAA33178 | NcLPMO9M | cellulose | C1, C4 | AA9 |

TABLE 2-continued

LPMOs (AA9, AA10 and AA11 families of the CAZy classification)

| Organism | Uniprot ref. | GenBank ref. | Other names | Substrate specificity | Known selectivity | Modularity |
|---|---|---|---|---|---|---|
| *N. crassa* | Q7SHI8 | EAA36362 | NcLPMO9C | cellulose hemicellulose | C4 | AA9-CBM1 |
| *N. crassa* | Q1K4Q1 | EAA26656 CAD70347 | NcLPMO9F | cellulose | C1 | AA9 |
| *N. crassa* | Q7SCJ5 | EAA34466 | NcU00836 | cellulose | C1 | AA9-CBM1 |
| *N. crassa* | Q7SCE9 | EAA34371.2 | NcAA13 | starch | C1 | AA13-CBM20 |
| *N. crassa* | Q7S439 | EAA30263 | NcU02240 | cellulose | C4 | AA9-CBM1 |
| *N. crassa* | Q7S111 | EAA29018 | NcU07760 | cellulose | C1, C4 | AA9-CBM1 |
| *P. chrysosporium* | H1AE14 | BAL43430 | PcLPMO9D | cellulose | C1 | AA9 |
| *P. anserina* | B2B629 | CAP73254 | PaGH61A PaLMPOB | cellulose | C1$^a$, C4$^a$ | AA9-CBM1 |
| *P. anserina* | B2AVF1 | CAP68375 | PaGH61B PaLMPO9A | cellulose | C1, C4 | AA9-CBM1 |
| *P. anserina* | B2ARG6 | CAP66744 | PaLPMO9D | cellulose | C1 | AA9 CBM1 |
| *P. anserina* | B2ATL7 | CAP67740 | PaLPMO9E | cellulose | C1 | AA9 CBM1 |
| *P. anserina* | B2B403 | CAP71839 | PaLPMO9F | cellulose | n.d | AA9 CBM1 |
| *P. anserina* | B2B5J7 | CAP73072 | PaLPMO9G | cellulose | n.d | AA9 CBM1 |
| *P. anserina* | B2ADG1 | CAP64476 | PaLPMO9H | cellulose | C1, C4 | AA9 CBM1 |
| *T. aurantiacus* | G3XAP7 | ABW56451 | TaGH61A | cellulose | C1 | AA9 |
| *T. terrestris* | G2RGE5 | AEO71030 | | cellulose | n.d. | AA9 |
| *T. reesei* | Q7Z9M7 | AAP57753 | | cellulose | n.d. | AA9 |
| *T. reesei* | O14405 | CAA71999 | Cel61A | cellulose | n.d. | AA9 |
| Bacteria | | | | | | |
| *Bacillus amyloliquefaciens* | E1UUV3 | CBI42985 | | n.d. | n.d. | AA10 |
| *Burkholderia pseudomallei* 1710b | Q3JY22 | ABA49030 | BURPS1710b_0114 (BpAA10A) | n.d. | n.d. | AA10 |
| *Bacillus licheniformes* | Q62YN7 | AAU22121 | | chitin | C1 | AA10 |
| *Caldibacillus cellulovorans* | Q9RFX5 | AAF22274 | β-1,4-mannanase (ManA) | n.d. | n.d. | AA10 |
| *Enterococcus faecalis* | Q838S1 | AAO80225 | EfLPMO10A | chitin | C1 | AA10 |
| *Hahella chejuensis* | Q2SNS3 | ABC27701 | LPMO (HcAA10-2; HCH_00807) | cellulose | nd | AA10 |
| *Serratia marcescens* | O83009 | AAU88202 | SmLPMO10A | chitin | C1 | AA10 |
| *Streptomyces coelicolor* | Q9RJC1 | CAB61160 | ScLPMO10B | cellulose chitin | C1, C4 | AA10 |
| *Streptomyces coelicolor* | Q9RJY2 | CAB61600 | ScLPMO10C | cellulose | C1 | AA10-CBM2 |
| *Thermobifida fusca* | Q47QG3 | AAZ55306 | TfLPMO10A | cellulose chitin | C1, C4 | AA10 |
| *Thermobifida fusca* | Q47PB9 | AAZ55700 | TfLPMO10B | cellulose | C1 | AA10-CBM2 |
| *V. cholerae* O1 | Q9KLD5 | AAF96709 | VcLPMO10B | n.d. | n.d. | AA10 |

The term "substrate specificity" is intended to mean the type of substrate cleaved (oxidative cleavage) by the corresponding LPMO enzyme.
The term "known selectivity" is intended to mean the carbon of the glucose ring oxidized by the corresponding LPMO enzyme.
The term "modularity" is intended to mean the CAZy class (AA9, 10 or 11) of the enzyme and the known presence of a conserved domain (CBM or X278).

The invention claimed is:

1. A process for producing nanocelluloses from a cellulose-based substrate comprising cellulose fibers, said process comprising the following successive steps:
one or more step(s) of enzymatic treatment of said cellulose-based substrate, by bringing it into contact with at least one cleavage enzyme consisting of enzymes belonging to the lytic polysaccharide monooxygenase (LPMO) family capable of carrying out an oxidative cleavage of said cellulose fibers in the presence of a donor electron,
wherein said at least one LPMO enzyme is purified from a culture supernatant of a fungus and/or produced in a heterologous system, wherein said at least one LPMO introduces, into the cellulose fibers, charged groups which create electrostatic repulsions, then at least one step of mechanical treatment of said cellulose-based substrate subjected to said one or more step(s) of enzymatic treatment, wherein said at least one step of mechanical treatment is chosen among mechanical treatments exerting a shear action, in order to delaminate said cellulose fibers and to obtain said nanocelluloses, wherein said oxidative cleavage of said cellulose fibers, catalyzed by said at least one LPMO, facilitates the delamination of these cellulose fibers during said at least one step of mechanical treatment.

2. The process for producing nanocelluloses as claimed in claim 1, wherein the LPMOs are chosen from the enzymes capable of carrying out a cleavage of the cellulose by oxidation of at least one of the carbon atoms in positions $C_1$, $C_4$ and $C_6$ of the glucose ring.

3. The process for producing nanocelluloses as claimed in claim 2, wherein the LPMOs are chosen from the AA9 and AA10 families of the CAZy classification.

4. The process for producing nanocelluloses as claimed in claim 1, wherein the LMPOs are chosen from the LPMOs derived from *Podospora anserina*.

5. The process for producing nanocelluloses as claimed in claim 4, wherein the LMPOs are chosen from PaLPMO9A (Genbank CAP68375), PaLPMO9B (Genbank CAP73254), PaLPMO9D (Genbank CAP66744), PaLPMO9E (Genbank CAP67740), PaLPMO9F (Genbank CAP71839), PaLPMO9G (Genbank CAP73072) and PaLPMO9H (Genbank CAP61476).

6. The process for producing nanocelluloses as claimed in claim 1, wherein the electron donor is chosen from ascorbate, gallate, catechol, reduced glutathione, lignin fragments and fungal carbohydrate dehydrogenases.

7. The process for producing nanocelluloses as claimed in claim 1, wherein the cellulose-based substrate is obtained from wood, a cellulose-rich fibrous plant, beetroot, citrus fruits, annual straw plants, marine animals, algae, fungi or bacteria.

8. The process for producing nanocelluloses as claimed in claim 1, wherein the cellulose-based substrate is chosen from chemical papermaking pulps.

9. The process for producing nanocelluloses as claimed in claim 8, wherein the cellulose-based substrate is chosen from chemical wood papermaking pulps.

10. The process for producing nanocelluloses as claimed in claim 9, wherein the cellulose-based substrate is chosen from at least one of the following chemical wood papermaking pulps:
bleached pulps,
semi-bleached pulps,
raw pulps,
bisulfite pulps,
sulfate pulps,
sodium hydroxide pulps,
kraft pulps.

11. The process for producing nanocelluloses as claimed in claim 1, wherein, following said at least one step of mechanical treatment, said process comprises a post-treatment step.

12. The process for producing nanocelluloses as claimed in claim 11, said wherein the process comprises a post-treatment step chosen from an acid treatment, an enzymatic treatment, an oxidation, an acetylation, a silylation, or else a derivatization of certain chemical groups borne by the nanocelluloses.

13. The process for producing nanocelluloses as claimed in claim 1, wherein the nanocelluloses obtained consist of cellulose nanofibrils and/or of cellulose nanocrystals.

14. The process for producing nanocelluloses as claimed in claim 1, wherein said at least one step of mechanical treatment, exerting a shear action, comprises at least a homogenization treatment.

15. The process for producing nanocelluloses as claimed in claim 1, wherein said at least one step of mechanical treatment, exerting a shear action, comprises at least a microfluidization treatment.

16. The process for producing nanocelluloses as claimed in claim 1, wherein said at least one step of mechanical treatment, exerting a shear action, comprises at least an abrasion treatment.

17. The process for producing nanocelluloses as claimed in claim 1, wherein said at least one step of mechanical treatment, exerting a shear action, comprises at least a cryomilling treatment.

\* \* \* \* \*